(12) United States Patent
Vanhoutte et al.

(10) Patent No.: US 10,053,502 B2
(45) Date of Patent: Aug. 21, 2018

(54) SELECTIVE INHIBITORS OF C-FOS AND THEIR ANTIPROLIFERATIVE PROPERTIES

(71) Applicants: INSERM (INSTITUT NATIONAL DE LA SANTÉ ET DE LA RECHERCHE MÉDICALE), Prais (FR); CENTRE NATIONAL DE LA RECHERCHE SCIENTIFIQUE—CNRS, Paris (FR)

(72) Inventors: Peter Vanhoutte, Paris (FR); Jocelyne Caboche, Paris (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/302,814

(22) PCT Filed: Apr. 8, 2015

(86) PCT No.: PCT/EP2015/057588
§ 371 (c)(1),
(2) Date: Oct. 7, 2016

(87) PCT Pub. No.: WO2015/155218
PCT Pub. Date: Oct. 15, 2015

(65) Prior Publication Data
US 2017/0029487 A1    Feb. 2, 2017

(30) Foreign Application Priority Data

Apr. 8, 2014  (EP) .................... 14305512

(51) Int. Cl.
| | | |
|---|---|---|
| *A61K 38/00* | (2006.01) |
| *C07K 14/82* | (2006.01) |
| *A61K 38/17* | (2006.01) |
| *C07K 14/47* | (2006.01) |

(52) U.S. Cl.
CPC .......... *C07K 14/82* (2013.01); *A61K 38/1764* (2013.01); *C07K 14/4705* (2013.01); *C12Y 207/11024* (2013.01); *A61K 38/00* (2013.01); *C07K 2319/10* (2013.01)

(58) Field of Classification Search
CPC ................ A61K 38/00; A61K 38/1764; C07K 14/4705; C07K 14/82; C07K 2319/10; C12Y 207/11024
See application file for complete search history.

(56) References Cited

U.S. PATENT DOCUMENTS

| | | |
|---|---|---|
| 2007/0066616 A1 | 3/2007 | Shapiro et al. |
| 2009/0186379 A1 | 7/2009 | Reed |
| 2009/0215680 A1 | 8/2009 | Caboche et al. |

FOREIGN PATENT DOCUMENTS

| | | |
|---|---|---|
| WO | WO 2005/007090 A2 | 1/2005 |
| WO | WO 2006/087242 A2 | 8/2006 |
| WO | WO 2012/016963 A1 | 2/2012 |

OTHER PUBLICATIONS

*International Search Report (PCT/ISA/210) dated Jun. 19, 2015, by the European Patent Office as the International Searching Authority for International Application No. PCT/EP2015/057588.
*Germä N A Gil et al., "Controlling Cytoplasmic c-Fos Controls Tumor Growth in the Peripheral and Central Nervous System", Neurochemical Research, Kluwer Academic Publishers-Plenum Publishers, NE, vol. 37, No. 6, Apr. 5, 2012, pp. 1364-1371.
*Gozes et al., "NAP Accelerates the Performance of Normal Rats in the Water Maze", Journal of Molecular Neuroscience, vol. 19, pp. 167-170, 2002.

*Primary Examiner* — Marcela M Cordero Garcia
(74) *Attorney, Agent, or Firm* — Buchanan Ingersoll & Rooney, PC

(57) ABSTRACT

Selective inhibitor of c-Fos and their antiproliferative properties The invention relates to selective inhibitor of c-Fos for use in the prevention and/or treatment of cancers and restenosis.

21 Claims, 10 Drawing Sheets

Figure 1:
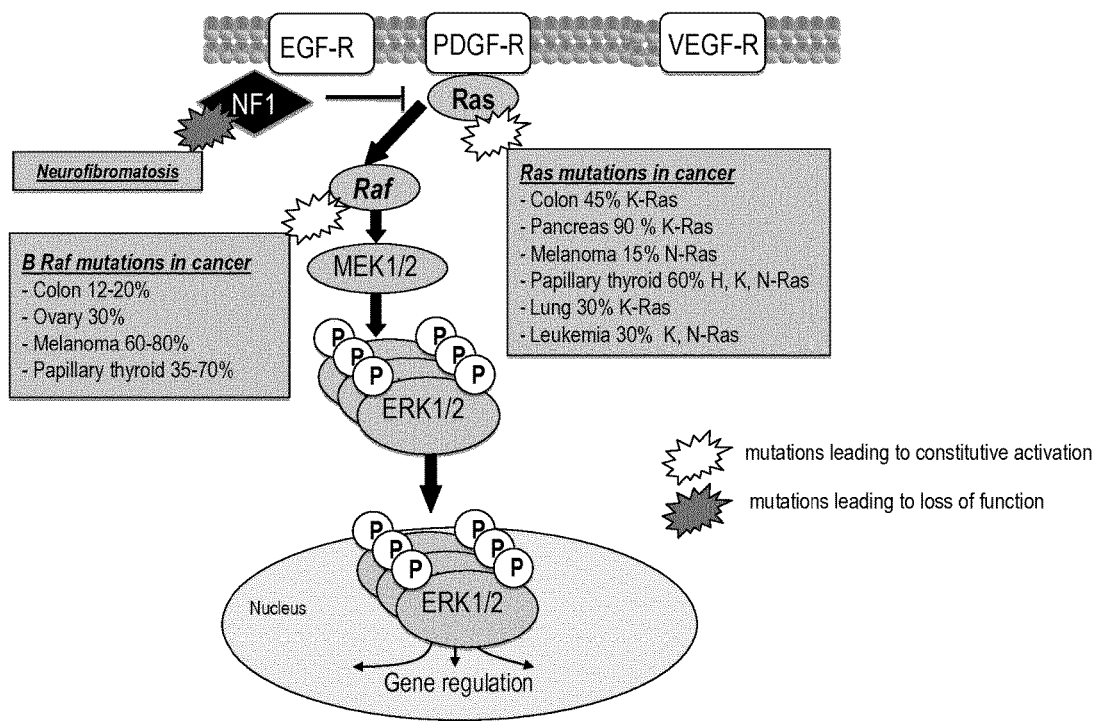

TAT-DEF-Fos is devoid of anti-proliferative properties on HCAEC

- Comparative effects of TAT-DEF-Elk-1, TAT-DEF-JunB, TAT-DEF-cFos and penetratin-DEF-cFos on MPNST

SEQUENCE LISTING

```
<160> NUMBER OF SEQ ID NOS: 39

<210> SEQ ID NO 1
<211> LENGTH: 19
<212> TYPE: PRT
<213> ORGANISM: Artificial Sequence
<220> FEATURE:
<223> OTHER INFORMATION: peptide

<400> SEQUENCE: 1

Cys Thr Thr Tyr Thr Ser Ser Phe Val Phe Thr Tyr Pro Glu Ala Asp
1               5                   10                  15

Ser Phe Pro

<210> SEQ ID NO 2
<211> LENGTH: 10
<212> TYPE: PRT
<213> ORGANISM: Artificial Sequence
<220> FEATURE:
<223> OTHER INFORMATION: penetrating sequence
```

```
<400> SEQUENCE: 2

Gly Arg Lys Lys Arg Gln Arg Arg
1               5                   10

<210> SEQ ID NO 3
<211> LENGTH: 16
<212> TYPE: PRT
<213> ORGANISM: Artificial Sequence
<220> FEATURE:
<223> OTHER INFORMATION: penetrating sequence

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: penetrating sequence

<400> SEQUENCE: 4

Arg Arg Arg Arg Arg Arg Arg
1               5

<210> SEQ ID NO 5
<211> LENGTH: 8
<212> TYPE: PRT
<213> ORGANISM: Artificial Sequence
<220> FEATURE:
<223> OTHER INFORMATION: penetrating sequence

<400> SEQUENCE: 5

Arg Arg Arg Arg Arg Arg Arg Arg
1               5

<210> SEQ ID NO 6
<211> LENGTH: 9
<212> TYPE: PRT
<213> ORGANISM: Artificial Sequence
<220> FEATURE:
<223> OTHER INFORMATION: penetrating sequence

<400> SEQUENCE: 6

Arg Arg Arg Arg Arg Arg Arg Arg Arg
1               5

<210> SEQ ID NO 7
<211> LENGTH: 10
<212> TYPE: PRT
<213> ORGANISM: Artificial Sequence
<220> FEATURE:
<223> OTHER INFORMATION: penetrating sequence

<400> SEQUENCE: 7

Arg Arg Arg Arg Arg Arg Arg Arg Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: penetrating sequence
```

```
<400> SEQUENCE: 8

Arg Arg Arg Arg Arg Arg Arg Arg Arg Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: penetrating sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 9

Xaa Arg Arg Arg Arg Arg Arg Arg
1               5

<210> SEQ ID NO 10
<211> LENGTH: 8
<212> TYPE: PRT
<213> ORGANISM: Artificial Sequence
<220> FEATURE:
<223> OTHER INFORMATION: penetrating sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 10

Arg Arg Arg Arg Arg Arg Arg Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: penetrating sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 11

Xaa Arg Arg Arg Arg Arg Arg Arg Xaa
1               5

<210> SEQ ID NO 12
<211> LENGTH: 14
<212> TYPE: PRT
<213> ORGANISM: Artificial Sequence
<220> FEATURE:
<223> OTHER INFORMATION: penetrating sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
```

```
<400> SEQUENCE: 12

Xaa Arg Arg Arg Arg Arg Arg Xaa Arg Arg Arg Arg Xaa
1               5                  10

<210> SEQ ID NO 13
<211> LENGTH: 23
<212> TYPE: PRT
<213> ORGANISM: Artificial Sequence
<220> FEATURE:
<223> OTHER INFORMATION: penetrating sequence

<400> SEQUENCE: 13

Gly Ala Tyr Asp Leu Asp Arg Arg Glu Arg Gln Ser Arg Leu Arg
1               5                   10                  15

Arg Arg Glu Arg Gln Ser Arg
            20

<210> SEQ ID NO 14
<211> LENGTH: 14
<212> TYPE: PRT
<213> ORGANISM: Artificial Sequence
<220> FEATURE:
<223> OTHER INFORMATION: penetrating sequence

<400> SEQUENCE: 14

Ser Arg Arg Ala Arg Arg Ser Pro Arg His Leu Gly Ser Gly
1               5                   10

<210> SEQ ID NO 15
<211> LENGTH: 16
<212> TYPE: PRT
<213> ORGANISM: Artificial Sequence
<220> FEATURE:
<223> OTHER INFORMATION: penetrating sequence

<400> SEQUENCE: 15

Leu Arg Arg Glu Arg Gln Ser Arg Leu Arg Arg Glu Arg Gln Ser Arg
1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: penetrating sequence

<400> SEQUENCE: 16

Val Lys Arg Gly Leu Lys Leu Arg His Val Arg Pro Arg Val Thr Arg
1               5                   10                  15

Met Asp Val

<210> SEQ ID NO 17
<211> LENGTH: 16
<212> TYPE: PRT
<213> ORGANISM: Artificial Sequence
<220> FEATURE:
<223> OTHER INFORMATION: penetrating sequence

<400> SEQUENCE: 17

Arg Lys Lys Arg Arg Arg Glu Ser Arg Lys Lys Arg Arg Glu Ser
1               5                   10                  15
```

```
<210> SEQ ID NO 18
<211> LENGTH: 7
<212> TYPE: PRT
<213> ORGANISM: Artificial Sequence
<220> FEATURE:
<223> OTHER INFORMATION: NLS sequence

<400> SEQUENCE: 18

Pro Lys Lys Lys Arg Lys Val
1               5

<210> SEQ ID NO 19
<211> LENGTH: 16
<212> TYPE: PRT
<213> ORGANISM: Artificial Sequence
<220> FEATURE:
<223> OTHER INFORMATION: NLS sequence

<400> SEQUENCE: 19

Lys Arg Pro Ala Ala Ile Lys Lys Ala Gly Gln Ala Lys Lys Lys Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: NLS sequence

<400> SEQUENCE: 20

Arg Gln Ala Arg Arg Asn Arg Arg Asn Arg Arg Arg Trp Arg
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: NES sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 21

Xaa Leu Xaa Xaa Xaa Leu Xaa Xaa Leu Xaa Leu Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: NES sequence
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 22

Xaa Leu Xaa Xaa Xaa Leu Xaa Xaa Leu Xaa Arg Xaa
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: NES sequence

<400> SEQUENCE: 23

Ala Leu Gln Lys Lys Leu Glu Glu Leu Glu Leu Asp
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: NES sequence

<400> SEQUENCE: 24

Thr Leu Trp Gln Phe Leu Leu Gln Leu Leu Leu Asp
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: NES sequence

<400> SEQUENCE: 25

Thr Leu Trp Gln Phe Leu Leu Gln Leu Leu Arg Glu
 1               5                  10

<210> SEQ ID NO 26
<211> LENGTH: 31
<212> TYPE: PRT
<213> ORGANISM: Artificial Sequence
<220> FEATURE:
<223> OTHER INFORMATION: peptide
```

```
<400> SEQUENCE: 26

Gly Arg Lys Lys Arg Arg Gln Arg Arg Pro Pro Cys Thr Thr Tyr
1               5                   10                  15

Thr Ser Ser Phe Val Phe Thr Tyr Pro Glu Ala Asp Ser Phe Pro
                20                  25                  30

<210> SEQ ID NO 27
<211> LENGTH: 31
<212> TYPE: PRT
<213> ORGANISM: Artificial Sequence
<220> FEATURE:
<223> OTHER INFORMATION: peptide

<400> SEQUENCE: 27

Gly Arg Lys Lys Arg Arg Gln Arg Arg Pro Pro Ser Pro Ala Lys
1               5                   10                  15

Leu Ser Phe Gln Phe Pro Ser Ser Gly Ser Ala Gln Val His Ile
                20                  25                  30

<210> SEQ ID NO 28
<211> LENGTH: 16
<212> TYPE: PRT
<213> ORGANISM: Artificial Sequence
<220> FEATURE:
<223> OTHER INFORMATION: peptide

<400> SEQUENCE: 28

Met Ala Gly Pro His Pro Val Ile Val Ile Thr Gly Pro His Glu Glu
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: docking domain

<400> SEQUENCE: 29

Phe Val Phe Thr Tyr Pro Glu Ala
1               5

<210> SEQ ID NO 30
<211> LENGTH: 10
<212> TYPE: PRT
<213> ORGANISM: Artificial Sequence
<220> FEATURE:
<223> OTHER INFORMATION: docking domain

<400> SEQUENCE: 30

Ser Phe Val Phe Thr Tyr Pro Glu Ala Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: docking domain

<400> SEQUENCE: 31

Ser Ser Phe Val Phe Thr Tyr Pro Glu Ala Asp Ser
1               5                   10
```

-continued

```
<210> SEQ ID NO 32
<211> LENGTH: 14
<212> TYPE: PRT
<213> ORGANISM: Artificial Sequence
<220> FEATURE:
<223> OTHER INFORMATION: docking domain

<400> SEQUENCE: 32

Thr Ser Ser Phe Val Phe Thr Tyr Pro Glu Ala Asp Ser Phe
1               5                   10

<210> SEQ ID NO 33
<211> LENGTH: 16
<212> TYPE: PRT
<213> ORGANISM: Artificial Sequence
<220> FEATURE:
<223> OTHER INFORMATION: docking domain

<400> SEQUENCE: 33

Tyr Thr Ser Ser Phe Val Phe Thr Tyr Pro Glu Ala Asp Ser Phe Pro
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: docking domain

<400> SEQUENCE: 34

Thr Tyr Thr Ser Ser Phe Val Phe Thr Tyr Pro Glu Ala Asp Ser Phe
1               5                   10                  15

Pro

<210> SEQ ID NO 35
<211> LENGTH: 18
<212> TYPE: PRT
<213> ORGANISM: Artificial Sequence
<220> FEATURE:
<223> OTHER INFORMATION: docking domain

<400> SEQUENCE: 35

Thr Thr Tyr Thr Ser Ser Phe Val Phe Thr Tyr Pro Glu Ala Asp Ser
1               5                   10                  15

Phe Pro

<210> SEQ ID NO 36
<211> LENGTH: 32
<212> TYPE: PRT
<213> ORGANISM: Artificial Sequence
<220> FEATURE:
<223> OTHER INFORMATION: pepsignal

<400> SEQUENCE: 36

Gly Arg Lys Lys Arg Arg Gln Arg Arg Pro Pro Cys Thr Thr Tyr
1               5                   10                  15

Thr Ser Ser Phe Val Phe Thr Tyr Pro Glu Ala Asp Ser Phe Pro Ser
                20                  25                  30

<210> SEQ ID NO 37
<211> LENGTH: 34
<212> TYPE: PRT
<213> ORGANISM: Artificial Sequence
<220> FEATURE:
<223> OTHER INFORMATION: pepsignal
```

```
<400> SEQUENCE: 37

Gly Arg Lys Lys Arg Arg Gln Arg Arg Pro Pro Thr Thr Pro Thr
1               5                   10                  15

Pro Pro Gly Gln Tyr Phe Tyr Pro Arg Gly Gly Ser Gly Gly Gly
            20                  25              30

Ala Gly

<210> SEQ ID NO 38
<211> LENGTH: 38
<212> TYPE: PRT
<213> ORGANISM: Artificial Sequence
<220> FEATURE:
<223> OTHER INFORMATION: pepsignal

<400> SEQUENCE: 38

Arg Gln Ile Lys Ile Trp Phe Trp Asn Arg Arg Met Lys Trp Lys Lys
1               5                   10                  15

Pro Pro Cys Thr Thr Tyr Thr Ser Ser Phe Val Phe Thr Tyr Pro Glu
            20                  25                  30

Ala Asp Ser Phe Pro Ser
            35

<210> SEQ ID NO 39
<211> LENGTH: 20
<212> TYPE: PRT
<213> ORGANISM: Artificial Sequence
<220> FEATURE:
<223> OTHER INFORMATION: docking domain c-Fos

<400> SEQUENCE: 39

Cys Thr Thr Tyr Thr Ser Ser Phe Val Phe Thr Tyr Pro Glu Ala Asp
1               5                   10                  15

Ser Phe Pro Ser
            20
```

SELECTIVE INHIBITORS OF C-FOS AND THEIR ANTIPROLIFERATIVE PROPERTIES

FIELD OF THE INVENTION

The invention relates to the use of selective inhibitors of c-Fos for treating abnormal proliferation in cancer and restenosis.

BACKGROUND OF THE INVENTION

Cancer is a broad group of various diseases, all involving uncontrolled cell growth. According to GLOBOCAN, on 2012 the number of new cases of cancer is estimated at 14.1 million and the number of death caused by cancer is estimated at 8.2 millions. In comparison, said numbers were estimated respectively at 12.7 and 7.6 millions in 2008. In 2008, cancer represented about 10% of total human deaths worldwide. Rates are rising while intensive investigations and researches for new therapeutic strategies are ongoing.

Several various therapeutic strategies have been proposed for overcoming cancer. One of them involves the MAP Kinase/ERK (Extracellular-signal Regulated) pathway and its inhibition, which is investigated in the hope of developing a new anticancer drug.

It has been shown that cancers are frequently associated with an aberrant activation of the ERK pathway. This is due to mutations encountered in a variety of malignancies that lead to an over-activation of Ras or Raf proteins upstream from ERK. Consequently, the inhibition of this pathway is intensely pursued as therapeutics.

However, targeting this pathway is challenging since ERK plays an essential role in homeostatic functions. This is probably due to the large number of distinct and even opposing cellular responses that are regulated by ERK. It follows that very few anticancer drugs targeting the ERK pathway have been validated at the clinical level for treating cancer. Indeed, the currently available ERK inhibitors act on the kinases upstream from ERK, including Raf or MEK, and as such act as total inhibitors of ERK activity towards all its substrates, without discrimination. This results in non-specific and important toxic side effects on cellular homeostasis, which is unacceptable in the treatment of patients suffering from cancer.

There is thus an unfulfilled need for new anti-cancer agents, which could efficiently target the ERK pathway, while being effective and having less undesirable side-effects.

The inventors have previously developed new strategies to overcome this challenge by targeting more specifically targets of interest downstream from ERK, rather than upstream of ERK. As disclosed in WO 2006/087242, the inventors have developed cell penetrating peptides that comprise an amino-acid sequence corresponding to the docking domain of a given substrate onto the kinase ERK (Extracellular-signal Regulated Kinase). Said peptides thus selectively interfere with either the DEJL or the DEF docking sites for ERK towards each of its substrates. Such specificity can be provided by the docking sites of ERK, which are necessary to provide selective recognition, interaction and phosphorylation of its substrates.

The DEF-domain docking site (Docking site for ERK, FXFP) is responsible for the binding of active ERK towards nuclear substrates, which are necessary for cell cycle progression. Another distinct domain is the D domain (or DEJL: Docking site for ERK and JNK, LXL), which is required for the recognition and activation of ERK effectors or kinases, such as Rsk or MSKs, but also ERK inhibition by its phosphatases (MKPs), or recognition and activation by MEKs.

The peptides previously developed by the inventors act downstream from ERK as selective inhibitors of one, and only one, ERK substrate. Their biological effects are thus more targeted and not toxic.

These peptides represent a new type of inhibitors that selectively impacts one target downstream of ERK, but leaves intact the global activity of ERK. This concept is based on the ability of ERK to bind to its downstream targets via specific docking domains, the DEJL and the DEF docking sites for ERK, that are crucial for the recognition, interaction and phosphorylation of substrates by activated ERK.

The inventors have designed a very specific peptide, namely TAT-DEF-c-Fos, to interfere with the interaction between ERK and the proto-oncogene c-Fos. This interaction is specific of the DEF domain, and leads to c-Fos phosphorylation, an important event for its stabilization and oncogenic properties. c-Fos is an immediate early gene, critically involved in cell transformation, highly expressed in different cancers, and is a pronostic marker of cancer progression.

Importantly, while there is increased amount of c-Fos expression in tumorigenic cells, c-Fos itself is rarely mutated in cancer, requiring dysfunction of the Ras/ERK signalling pathways for abnormal activity. c-Fos is also involved in the transition of tumorigenic cells into invasive and metastatic cells.

Surprisingly, the inventors have thus shown that the TAT-DEF-c-Fos, has anti-proliferative and anti-invasive properties on specific human cell lines.

Therefore, they developed a highly promising therapeutic strategy on pathologies associated with aberrant cell proliferation and invasion including cancers and metastasis.

SUMMARY OF THE INVENTION

In a first aspect, the invention relates to a selective inhibitor of c-Fos for use in the prevention and/or treatment of a cancer
- caused by or involving a mutation in the Ras/ERK pathway; and/or
- associated with an increased production of c-Fos;

wherein said selective inhibitor of c-Fos is a peptide comprising:
- at least one cell penetrating sequence; and
- an amino acid sequence corresponding to a docking domain sequence of c-Fos comprising SEQ ID NO: 29 (FVFTYPEA).

Preferably, said cancer is selected in the group consisting of colon cancer, pancreatic, cancer, melanoma, ovary cancer, lung cancer, thyroid cancer, leukaemia, juvenile myelomonocytic leukaemia, glioma, neurofibroma, cervical hepatocarcinoma, breast cancer, osteosarcoma and endometrial cancer.

In a second aspect, the invention relates to a selective inhibitor of c-Fos for use in a method of preventing metastasis, wherein said selective inhibitor of c-Fos is a peptide comprising:
- at least one cell penetrating sequence, and
- an amino acid sequence corresponding to a docking domain sequence of c-Fos comprising SEQ ID NO: 29 (FVFTYPEA).

In a third aspect, the invention relates a selective inhibitor of c-Fos for use for inhibiting and/or preventing proliferation of cells, preferably vascular smooth muscle cells, on a stent,
wherein said selective inhibitor of c-Fos is a peptide comprising:
  at least one cell penetrating sequence, and
  an amino acid sequence corresponding to a docking domain sequence of c-Fos comprising SEQ ID NO: 29 (FVFTYPEA),
wherein said stent is used for treating a patient suffering from a cardiovascular disease.

In a fourth aspect, the invention relates to a selective inhibitor of c-Fos for use for treating and/or preventing neurofibromatosis, wherein said selective inhibitor of c-Fos comprises at least one cell penetrating sequence, and an amino acid sequence corresponding to a docking domain sequence of c-Fos comprising SEQ ID NO: 29 (FVFTYPEA).

DETAILED DESCRIPTION OF THE INVENTION

Definitions

As used herein, the term "peptide" refers to an amino acid sequence having less than 100 amino acids. As used herein, the term "peptide" encompasses amino acid sequences having less than 90 amino acids, less than 80 amino acids, less than 70 amino acids, less than 60 amino acids, or less than 50 amino acids. Preferably, said amino acid sequence comprises 20, 21, 22, 23, 24, 25, 50, 75, or 100 amino acids.

As used herein, the term "treating" a disorder or a condition refers to reversing, alleviating or inhibiting the process of one or more symptoms of such disorder or condition. The term "preventing" a disorder or condition refers to preventing one or more symptoms of such disorder or condition.

A "therapeutically effective amount" as used herein is intended for a minimal amount of active agent, which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

As used herein, the expressions "peptide of the invention" or "selective inhibitor of c-Fos" refer to an inhibitor of c-Fos phosphorylation. More precisely, said expressions refer to an interfering peptide towards ERK and c-Fos interaction. Said peptide comprises:
  at least one cell penetrating sequence, and
  an amino acid sequence corresponding to a docking domain sequence of c-Fos.
    Said docking domain sequence is a DEF docking domain sequence of c-Fos.
Preferably, said amino acid sequence corresponding to a docking domain sequence of c-Fos is selected in the group consisting of:

(FVFTYPEA); SEQ ID NO: 29

(SFVFTYPEAD); SEQ ID NO: 30

(SSFVFTYPEADS); SEQ ID NO: 31

(TSSFVFTYPEADSF); SEQ ID NO: 32

(YTSSFVFTYPEADSFP); SEQ ID NO: 33

(TYTSSFVFTYPEADSFP); SEQ ID NO: 34

(TTYTSSFVFTYPEADSFP); SEQ ID NO: 35

(CTTYTSSFVFTYPEADSFP); SEQ ID NO: 1
and (CTTYTSSFVFTYPEADSFPS). SEQ ID NO: 39

Preferably, said amino acid sequence corresponding to a docking domain sequence of c-Fos is SEQ ID NO: 1 (CTTYTSSFVFTYPEADSFP). More preferably, said amino acid sequence corresponding to a docking domain sequence of c-Fos is SEQ ID NO: 39 (CTTYTSSFVFTYPEADSFPS).

The peptide of the invention selectively impacts the downstream target c-Fos, but leaves intact the global ERK activity. Preferably, said peptide is the specific peptide depicted in SEQ ID NO: 26. More preferably, said peptide is the specific peptide depicted in SEQ ID NO: 36.

In the context of the invention, said peptide is referred to as a "selective inhibitor of c-Fos" or a "selective interfering peptide towards ERK and c-Fos interaction".

As used herein, the term "c-Fos" or "Fos" refers to a proto-oncogene that is the human homolog of the retroviral oncogene v-Fos. c-Fos is 380 amino acid protein. The sequence of c-Fos is available online under the accession number GenBank: CAA24756.1. This immediate early gene has been implicated in cell cycle progression. c-Fos and its implication in cancer is disclosed in the publication Healy et al., *Immediate early response genes and cell transformation*, Pharmacology & Therapeutics, Volume 137, Issue 1, January 2013, Pages 64-77.

As used herein, the expression "MAP kinase" or "mitogen-activated protein kinase" (MAPK), refers to a family of widely expressed protein kinases that act intracellularly to regulate multiple functions, including meiosis, mitosis, differentiation and apoptosis. The MAPK "extracellular-signal-regulated kinases", "ERK" pathway involves several upstream intracellular partners, including the small-GTP exchanging factor Ras, which activates members of the c-Raf family, followed by mitogen-activated protein kinase (abbreviated as MKK, MEK, or MAP2K) and then ERK1/2.

Hormones, growth factors and even mechanical/physical stimuli usually activate membrane receptors that further activate intracellular signaling pathways including the MAPK/ERK pathway. The first intracellular event in the activation of this pathway is a small GTP binding protein, such as Ras, which in turn activate a cascade of phosphorylation events within the cytoplasm of cells. This cascade includes MAP3kinase (MAP3K, usually Raf kinases: Raf-1, A-Raf and B-Raf), which can activate the MAPKK components (MEK1 and MEK2: MEKs), and then MAPK (ERK1, ERK2). In turn activated ERKs can phosphorylate hundreds of distinct substrates that are involved in many fundamental cellular responses, including differentiation, proliferation, morphology determination and more. The specificity of ERK on these cellular responses, and hence biological functions, intimately depends on selective substrates, which can be membranal, cytoplasmic or nuclear. In this way it is now well established that once activated ERK can translocate to the nucleus, depending on the strength and the duration of the stimulation. Herein, ERK can phosphorylate (i.e activate) transcription factors that have been implicated in cell cycle progression, including the transcription factors Elk-1 and c-Fos. The specific signaling pathway and mutations in human cancer is summarized in FIG. 1.

Figure 2:
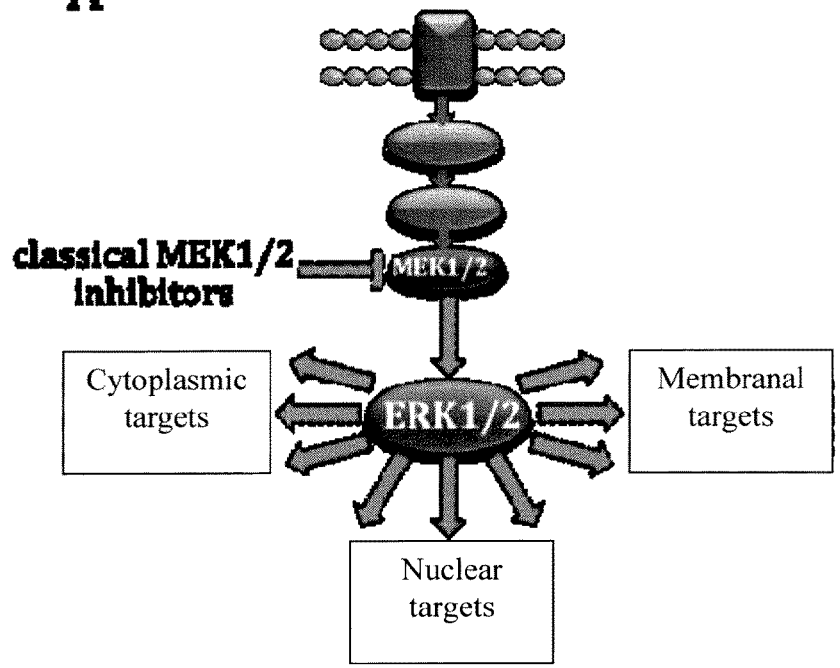
Figure 2:
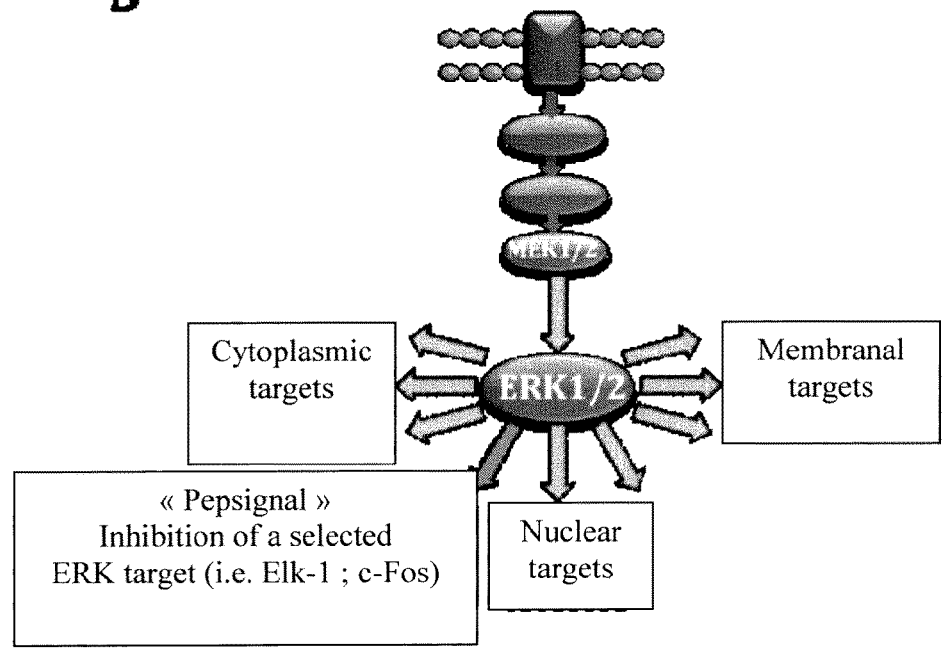

As used herein, the term "pepsignals" refers to the peptides developed by the inventors and which are disclosed in WO 2006/087242. The concept underlying these peptides is depicted in FIG. 2.

Said peptides act downstream from ERK. This is based on the ability of ERK to bind to its downstream targets via specific docking domains, the DEJL (for Docking site for ERK and JNK, LXL) and the DEF (Docking site for ERK, FXFP) docking sites for ERK, that are crucial for the recognition, interaction and phosphorylation of substrates by activated ERK.

Thus, "pepsignals" mimic the DEF docking domain of a given substrate towards ERK, and as such have a very specific inhibitory impact on a given substrate of interest, without affecting the global activity of ERK.

The peptide of the invention TAT-DEF-c-Fos is a "pepsignal".

As intended herein, the expression "cancer" relates to a disease characterized by an uncontrolled cell growth and invasion of adjacent tissues. The abnormal cells often are referred to as neoplastic cells which are transformed cells that can form a solid tumor. As used herein, the term cancer refers to any stage of development of the disease.

The term "tumor" refers to an abnormal mass or population of cells (i.e. two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

As used herein, "restenosis" refers to the reduction in lumen diameter after percutaneous coronary intervention (PCI). Restenosis is the result of arterial damage with subsequent neointimal tissue proliferation. Basically, it is due to the inflammation occurring after angioplasty and stent implantation in the treatment of cardiovascular diseases. Restenosis is characterized by a proliferation of vascular smooth muscle cells as well as a migration of said cells due to the inflammation.

The Invention

In a first aspect, the inventions relates to selective inhibitor of c-Fos for use in the prevention and/or treatment of a cancer
   caused by or involving a mutation in the Ras/ERK pathway; and/or
   associated with an increased production of c-Fos;
wherein said selective inhibitor of c-Fos is a peptide comprising:
   at least one cell penetrating sequence; and
   an amino acid sequence corresponding to a DEF docking domain of c-Fos towards ERK, preferably an amino acid sequence corresponding to a docking domain sequence of c-Fos comprising SEQ ID NO: 29 (FVFTYPEA).

The inventors have shown that the peptide of the invention present promising inhibitory properties in cell proliferation, migration and malignity on different cell types. In addition, the inventors have shown that the peptide of the invention has antiproliferative effects whereas peptides targeting other substrates, including the peptide TAT-DEF-Elk-1 as depicted in SEQ ID NO: 27 or TAT-DEF-JunB as depicted in SEQ ID NO: 37 didn't show an effect as important. In particular, the peptide TAT-DEF-Elk-1 had no effect on either vSMC, NIH3T3 or HCAEC, and a slight inhibitory effect on MPNST (without reaching IC50).

The inventors thus developed a peptide targeting specifically the DEF domain of c-Fos, which proves to have beneficial effects on the outcome of different proliferating cells. In addition, this peptide was found to be devoid of any toxicity and to have important anti-invasive properties, as tested in the wound-healing test, thus indicating it can prevent metastasis.

More specifically, they have surprisingly shown that said peptide has anti-proliferative properties on vascular smooth muscle cells of human origin (vSMC), malignant peripheral nerve sheath tumors from NF1 patients and fibroblasts. Said effect was not found in endothelial cells of human origin (HCAEC). Hence, the peptide of the invention is useful for inhibiting and/or preventing the proliferation of a cell selected in the group of vascular smooth muscle cells, fibroblasts, and nerve sheath cells.

In one embodiment, the targeted cancer is caused by or involves a mutation in the Ras/ERK pathway. Preferably, said mutation in the Ras/ERK pathway is a mutation of any components of this pathway, more preferably Ras, Raf and NF1. The incidence of and type of cancers in relation with these mutations is summarized FIG. 1. Typically, said mutations of Ras or Raf lead to their constitutive activity towards ERK, and hence aberrant activation of ERK. Typically, said mutations of NF1 leads to an overactivation of Ras. Consequently, relevant mutations in the Ras/ERK pathway are mutations of Ras, Raf and NF1.

"Ras" is a notable member of the large family of GTPases, proteins that bind and hydrolyze GTP. First discovered as transforming oncogenes of murine sarcoma viruses, three highly related 21 kDa mammalian proteins, Harvey-Ras (H-Ras), Kirsten-Ras (K-Ras), and Neuroblastoma-Ras (N-Ras) have been identified.14 Activating mutations of these Ras isoforms, which impair GTPase activity and stabilize the GTP bound state, or of their downstream effectors, are found in nearly one-third of all human cancers, making these oncoproteins among the most potent transforming polypeptides known.

Ras family members are anchored to the cytoplasmic face of the plasma membrane by C-terminal farnesylation. This localization to the inner leaflet brings Ras into close proximity with SOS, stimulating the exchange of GDP bound to Ras with GTP from the cytosol. This exchange activates Ras conformationally, allowing it to interact with a number of downstream effectors.

Within the ERK signaling cascade, active Ras functions as an adaptor that binds to effector Raf Murine Sarcoma Viral Oncogene Homolog (Raf) kinases with high affinity, causing their translocation to the cell membrane, where Raf activation takes place via Prohibitin (PHB).

Non-limiting list of cancers caused by or involving a mutation in Ras includes colon cancer, pancreatic cancer, melanoma, thyroid cancer, lung cancer and leukaemia.

"Raf" is a serine/threonine protein kinase, catalyzing the phosphorylation of hydroxyl groups on specific serine and threonine residues. Mammals possess three Raf proteins, ranging from 70 to 100 kDa in size:
   Raf-1, which is ubiquitously expressed;
   A-Raf, found in cartilage, intestine, heart, spleen, thymus, cerebellum, and urogenital tissues;

B-Raf, present in multiple isoforms is expressed in most tissues with high expression in neuronal tissue.

Recruitment to the plasma membrane by GTP-bound Ras is the initiating event in Raf activation. The effector domain of Ras binds Raf at two locations in the MAP3K's N-terminus, the Ras-binding domain (RBD) and the cysteine-rich domain (CRD), with binding at both sites necessary for activation.

Different Ras isoforms appear to activate Raf with varying ability, despite binding in vitro with comparable affinity. For example, K-Ras both recruits Raf-1 to the plasma membrane more efficiently, and activates the recruited Raf-1 more potently than H-Ras. It has also been suggested that B-Raf is the primary target of oncogenic Ras isoforms. Activating mutations of B-raf have been reported in approximately 50% of malignant melanomas.

Non-limiting list of cancers caused by or involving a mutation in Raf includes colon cancer, ovary cancer, melanoma, and thyroid cancer.

Consequently, cancers caused by or involving a mutation in Ras or Raf include colon cancer, pancreatic cancer, melanoma, thyroid cancer, lung cancer and leukaemia, and ovary cancer.

"NF1" encodes the protein neurofibromin, which is a negative regulator of the ras signal transduction pathway.

Mutations in NF1 have one of the greatest frequencies of spontaneous mutation in the whole human genome. It is a tumor suppressor, with expression detected in various cells, mainly in melanocytes, neurons, Schwann cells and glial cells. Due to its anti-tumoral function, inactivation of NF1 protein leads to the growth of several neoplasms, concerning mainly skin and central nervous system (CNS). Skin tumors are actually malignances of the peripheral nervous system (PNS) and include cutaneous, subcutaneous and plexiform neurofibromas. Neurofibroma is a nerve sheath tumor in the peripheral nervous system.

In the central nervous system, the most frequently occurring tumors are gliomas. Non-limiting list of cancers caused by or involving a mutation in NF1 includes glioma, juvenile myelomonocytic leukaemia and neurofibroma.

Consequently, cancers caused by or involving a mutation in the Ras/ERK pathway especially Ras, Raf and NF1 include colon cancer, pancreatic cancer, melanoma, ovary cancer, lung cancer, thyroid cancer, leukaemia, juvenile myelomonocytic leukemia, glioma and neurofibroma.

In another embodiment, the targeted cancer is associated with an increased production of c-Fos. Said increase leads to an accumulation of c-Fos at the cellular level, said accumulation being abnormal.

Non-limiting list of cancers associated with an increased production of c-Fos includes cervical hepatocarcinoma, pancreatic cancer, breast cancer, osteosarcoma, and endometrial cancer.

Consequently, the invention relates to a selective inhibitor of c-Fos for use for preventing and/or treating a cancer selected in the group consisting of colon cancer, pancreatic cancer, melanoma, ovary cancer, lung cancer, thyroid cancer, leukaemia, juvenile myelomonocytic leukaemia, glioma, neurofibroma, cervical hepatocarcinoma, breast cancer, osteosarcoma and endometrial cancer, wherein said selective inhibitor of c-Fos comprises at least one cell penetrating sequence, and an amino acid sequence corresponding to a docking domain sequence of c-Fos comprising SEQ ID NO: 29 (FVFTYPEA).

The invention further relates to a selective inhibitor of c-Fos for use for inhibiting and/or preventing proliferation of a cell selected in the group consisting of vascular smooth muscle cells, fibroblasts, and nerve sheath cells, wherein said selective inhibitor of c-Fos comprises at least one cell penetrating sequence, and an amino acid sequence corresponding to a docking domain sequence of c-Fos comprising SEQ ID NO: 29 (FVFTYPEA).

Finally, the inventors have shown that the peptide of the invention shows antiproliferative effect in a lower dose, compared to classical inhibitors of proliferation used in prior art, such as Rapamycin or Paclitaxel. The peptide of the invention is thus highly efficient, at a lower dose, which limits the potential side effects.

In a second aspect, the invention pertains in a selective inhibitor of c-Fos for use in a method of preventing metastasis, wherein said selective inhibitor of c-Fos is a peptide comprising:
at least one cell penetrating sequence; and
an amino acid sequence corresponding to a docking domain sequence of c-Fos comprising SEQ ID NO: 29 (FVFTYPEA).

As used herein, the term "metastasis" refers to a process in which cancer cells spread from one organ or tissue to another non-adjacent organ or tissue. Typically, the spread of the cancer cells occurs via lymph or blood.

Because of its properties of inhibition of invasiveness, the peptide of the invention constitutes a highly promising strategy for preventing metastasis.

The inventors corroborated this result in a wound-healing test. Surprisingly, the inventors have shown a beneficial effect of the peptide of the invention, whereas the global MEK inhibitor (namely U0126) was found not appropriate.

Preferably, the peptide of the invention prevents from the spread of cancer cells chosen among cancer cells of colon cancer, pancreatic cancer, melanoma, ovary cancer, lung cancer, thyroid cancer, leukaemia, juvenile myelomonocytic leukaemia, glioma, neurofibroma, cervical hepatocarcinoma, breast cancer, osteosarcoma and endometrial cancer.

In a third aspect, the invention relates to selective inhibitor of c-Fos for use for inhibiting and/or preventing proliferation of vascular smooth muscle cells, on a stent, wherein said selective inhibitor of c-Fos is a peptide comprising:
at least one cell penetrating sequence; and
an amino acid sequence corresponding to a docking domain sequence of c-Fos comprising SEQ ID NO: 29 (FVFTYPEA);
wherein said stent is used for treating a patient suffering from a cardiovascular disease.

Typically, said stent was used in a patient who suffered or suffers from cardiovascular diseases, preferably coronary artery disease. In another embodiment, the patient went through or goes through an angioplasty procedure.

Preferably, said stent is a drug eluting stent. As used herein, "drug-eluting stent" refers to a stent that relates a substance that block cell proliferation. In the context of the invention, said substance is the peptide as disclosed herein.

It is well known that the use of a stent may lead to restenosis. In this specific context, the peptide of the invention is highly useful for inhibiting and/or preventing proliferation of vascular smooth muscle cells and its invasiveness into the stent.

In this very specific embodiment, the peptide of the invention can be used as a drug-eluting stent, typically in an angioplasty procedure.

In another embodiment, said peptide does not interfere with proliferation of endothelial cells.

Consequently, the inventors have thus developed a highly promising peptide, which may be used for treating and/or preventing cancer, used for inhibiting pathological cell invasiveness and metastatic processes, and inhibiting and/or preventing proliferation of vascular smooth muscle cells in the patient who went through an angioplasty or a stent implantation, for example in the context of the treatment of a cardiovascular disease.

Said peptide proved to:
- have anti-proliferative properties on vascular smooth muscle cells, fibroblasts, and nerve sheath cells;
- be devoid of toxicity; and
- inhibit invasiveness.

In a fourth aspect, the invention further relates to a selective inhibitor of c-Fos for use for treating and/or preventing neurofibromatosis, wherein said selective inhibitor of c-Fos comprises at least one cell penetrating sequence, and an amino acid sequence corresponding to a docking domain sequence of c-Fos comprising SEQ ID NO: 29 (FVFTYPEA). Preferably, said inhibitor is used for treating and/or preventing peripheral nerve sheath tumors.

The inventors have thus shown the efficacy of the peptide of the invention on malignant NF1 cell proliferation, preferably peripheral nerve sheath tumors.

Besides the role of the peptide in tumors, said result corroborate that the peptide of the invention can be useful in a method of treatment of neurofibromatosis.

As used herein, "neurofibromatosis" refers to a number of inherited conditions that are clinically and genetically distinct and carry a high risk of tumor formation, particularly in the central and peripheral nervous system. The neurofibromatosis can be classified as follows:
- Neurofibromatosis type I, in which the nerve tissue grows tumors (neurofibromas) that may be benign and may cause serious damage by compressing nerves and other tissues.
- Neurofibromatosis type II, in which bilateral acoustic neuromas (tumors of the vestibulocochlear nerve or cranial nerve 8 (CN VIII) also known as Schwannoma) develop, often leading to hearing loss,
- Schwannomatosis, in which painful schwannomas develop on cranial, spinal and peripheral nerves.

As used herein, the term neurofibromatosis includes all of the above mentioned category of conditions. Preferably, in the context of the invention, said neurofibromatosis is neurofibromatosis I.

Preferably, the cell penetrating sequence of the peptide of the invention is chosen in the group comprising:
- HIV-TAT sequence (SEQ ID NO: 2);
- Penetratin (SEQ ID NO: 3);
- an amino acid sequence of 7 to 11 arginine (SEQ ID NO: 4 to 8);
- a X7/11R sequence wherein said sequence is a 7 to 25 amino acid sequence, preferably a 7 to 20 amino acid sequence, comprising 7 to 11 arginine randomly positioned in the sequence such as SEQ ID NO: 9 to 12; and
- a sequence derived from the Vectocell® as cell penetrating sequences described in De Coupade et al. Biochem J (2005) 390, 407-418 et WO01/64738, such as SEQ ID NO: 13 to 17.

Non-limiting examples of X7/11R sequences and DPV sequences are given in the following table.

| | | |
|---|---|---|
| SEQ ID NO: 2 | GRKKRRQRRR | HIV-TAT |
| SEQ ID NO: 3 | RQIKIVVFQNRRMKWKK | Penetratine |
| SEQ ID NO: 4 | RRRRRRR | 7R |
| SEQ ID NO: 5 | RRRRRRRR | 8R |
| SEQ ID NO: 6 | RRRRRRRRR | 9R |
| SEQ ID NO: 7 | RRRRRRRRRR | 10R |
| SEQ ID NO: 8 | RRRRRRRRRRR | 11R |
| SEQ ID NO: 9 | XRRRRRRR | X7R (example) |
| SEQ ID NO: 10 | RRRRRRRX | X7R (other example) |
| SEQ ID NO: 11 | XRRRRRRRX | X7R (other example) |
| SEQ ID NO: 12 | XRRRRRRXRRRRRX | X11R (other example) |
| SEQ ID NO: 13 | GAYDLDRRREROSRLRRRERQSR | DPV15b |
| SEQ ID NO: 14 | SRRARRSPRHLGSG | DPV10 |
| SEQ ID NO: 15 | LRRERQSRLRRERQSR | DPV15 |
| SEQ ID NO: 16 | VKRGLKLRHVRPRVTRMDV | DPV1047 |
| SEQ ID NO: 17 | RKKRRRESRKKRRRES | DPV3 |

In one embodiment of the invention, the cell penetrating sequence and the docking domain of the peptide inhibitors of the invention can be linked by chemical coupling in any suitable manner known in the art.

In another embodiment of the invention, said selective inhibitor of c-Fos further comprise a nuclear localization signal (NLS) sequence and/or a nuclear export sequence (NES) sequence.

Said NLS and NES sequences are well known in the art and comprise 2 to 20 amino acids, preferably 3, 4, 5, . . . , 18, 19 or 20 amino acids.

In one embodiment, said NLS and NES sequences are chosen in the following table.

| | | origin |
|---|---|---|
| NLS sequence | | |
| SEQ ID NO: 18 | PKKKRKV | SV40 large T-antigen |
| SEQ ID NO: 19 | KRPAAIKKAGQAKKKK | Nucleoplasmin |
| SEQ ID NO: 20 | RQARRNRRNRRRRWR | HIV1Rev |
| SEQ ID NO: 2 | GRKKRRQRRR | HIV-TAT |
| SEQ ID NO: 3 | RQIKIWFQNRRMKWKK | Penetratin |
| SEQ ID NO: 4 | RRRRRRR | 7R |
| SEQ ID NO: 5 | RRRRRRRR | 8R |
| SEQ ID NO: 6 | RRRRRRRRR | 9R |
| SEQ ID NO: 7 | RRRRRRRRRR | 10R |
| SEQ ID NO: 8 | RRRRRRRRRRR | 11R |

-continued

| | NES sequence | origin |
|---|---|---|
| SEQ ID NO: 21 | XLXXXLXXLXLX | Elk-1 type consensus |
| SEQ ID NO: 22 | XLXXXLXXLXRX | Net type consensus |
| SEQ ID NO: 23 | ALQKKLEELELD | MAPKK |
| SEQ ID NO: 24 | TLWQFLLQLLLD | Net |
| SEQ ID NO: 25 | TLWQFLLQLLRE | Elk-1 |

In another embodiment, the selective inhibitor of c-Fos further comprise an enzymatic cleavage site, allowing to the cleavage in a cell between the cell penetrating sequence and the rest of the sequence of the peptide inhibitor.

In one embodiment, said enzymatic cleavage site comprises two consecutive cystein residues, allowing the intracellular cleavage by cytoplasmic glutathione.

In a preferred embodiment, said selective inhibitor of c-Fos has for sequence SEQ ID NO: 26 (GRKKRRQRRRP-PCTTYTSSFVFTYPEADSFP).

Thus, in one embodiment of the invention, the selective inhibitor of c-Fos consists essentially of an amino acid sequence according to SEQ ID NO: 26.

Alternatively, said selective inhibitor of c-Fos has for sequence SEQ ID NO: 36 (GRKKRRQRRRPPCTTYTSS-FVFTYPEADSFPS).

Thus, in another embodiment of the invention, the selective inhibitor of c-Fos consists essentially of an amino acid sequence according to SEQ ID NO: 36.

According to the invention, "consisting essentially of" shall mean that a peptide according to the present invention, in addition to the sequence according to any of SEQ ID No. 26, contains additional N- and/or C-terminally located stretches of amino acids that are not necessarily forming part of the peptide, which functions as the core sequence of the peptide.

In one embodiment of the invention, the amino acids that make up the peptide inhibitors are L enantiomers. In another embodiment of the invention, one or more amino acids of the peptide sequence can be replaced with its D enantiomer. In another embodiment of the invention, the peptide inhibitor is all D retro-inverso version of the peptide sequence.

The peptide inhibitors of the invention can be polymers of L-amino acids, D-amino acids, or a combination of both. For example, the peptides are D retro-inverso peptides. The term "retro-inverso isomer" refers to an isomer of a linear peptide in which the direction of the sequence is reversed and the chirality of each amino acid residue is inverted. The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Said peptide inhibitor of c-Fos may be obtained by conventional techniques known in the art. For example, said peptide inhibitors may be obtained by chemical synthesis, such as conventional solid phase synthesis or liquid phase synthesis. Solid phase synthesis using Boc (t-butyloxycarbonyl) or Fmoc (9-fluorenylmethoxycarbonyl) as the amino protecting group is suitable.

Said peptide inhibitors may also be biosynthesized by genetic engineering methods. This approach is suitable when producing polypeptides with relatively long peptide chains. That is, DNA is synthesized with a nucleotide sequence (including ATG initiation codon) coding for the amino acid sequence of the desired inhibitor peptide. A recombinant vector having a gene expression construct consisting of this DNA together with the various regulatory elements (including promoters, ribosome binding sites, terminators, enhancers, and various cis-elements for controlling expression level) required for expressing the amino acid sequence in host cells is then constructed according to the host cells. A common technique is to introduce this recombinant vector into specific host cells (such as yeast cells, insect cells, plant cells, bacterial cells or animal (mammal) cells), and then culture these host cells, or a tissue or organism containing these cells, under specific conditions. In this way, the target polypeptide can be expressed and produced in the cells. The polypeptide is then isolated and purified from the host cells (or from medium if it is excreted) to thereby obtain the desired inhibitor peptide. Methods conventionally used in the art can be adopted for constructing the recombinant vector and introducing the constructed vector into host cells. For example, a fused protein expression system can be used in order to achieve efficient, high-volume production in host cells. That is, a gene (DNA) coding for the amino acid sequence of the inhibitor peptide is chemically synthesized, and this synthetic DNA is introduced into a suitable site in a suitable fused protein expression vector (for example, a GST (Glutathione S-transferase) fused protein expression vector such as a Novagen pET series or Amersham Biosciences pGEX series vector). Host cells (typically *E. coli*) are then transformed with this vector. The resulting transformant is cultured to prepare the target-fused protein. The protein is extracted and purified. The resulting purified fused protein is cleaved with a specific enzyme (protease), and the released target peptide fragment is collected by a method such as affinity chromatography. The inhibitor peptide of the invention can be produced using such a conventional fused protein expression system (using for example a GST/His system from Amersham Biosciences). Alternatively, template DNA (that is, a synthetic DNA fragment comprising a nucleotide sequence coding for the amino acid sequence of the inhibitor peptide) for a cell-free protein synthesis system can be constructed, and the target polypeptide can be synthesized in vitro by means of a cell-free protein synthesis system using various compounds (ATP, RNA polymerase, amino acids, etc.) necessary for peptide synthesis.

Nucleic acid sequences encoding the selective inhibitor of c-Fos as described here above may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Expression vectors are also provided for recombinant expression of one or more selective inhibitor(s) of c-Fos as defined above. The term "expression vector" is used herein to designate either circular or linear DNA or RNA, which is either double-stranded or single-stranded. It further comprises at least one nucleic acid as described here above to be transferred into a host cell or into a unicellular or multicellular host organism.

The expression vector preferably comprises a nucleic acid encoding one or more selective inhibitor(s) of c-Fos as defined above. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, or matrix/scaffold attachment. In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more inventive nucleic acid sequences, and that is structurally identified by the presence of a binding site for DNA-dependent RNA-polymerase and of other DNA sequences, which interact to regulate promoter function. A functional expression-promoting fragment of a promoter is a shortened or truncated promoter sequence retaining the activity as a promoter. Promoter activity may be measured by any assay known in the art.

An "enhancer region" as used herein, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-a-vis the gene to be expressed, and may be enhancing, augmenting, improving, or ameliorating expression of more than one promoter. Promoter/enhancer sequences as defined above for the inventive expression vector, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter, or the glial fibrillary acidic protein promoter. Alternatively, or in addition, they may include animal transcriptional control regions.

Additionally, the expression vector may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD).

Exemplary expression vectors or their derivatives suitable for the invention particularly include, e.g. human or animal viruses (e.g. retrovirus, adenovirus, adeno-associated virus, herpes virus, vaccinia virus, poxvirus, poliovirus; lentivirus); insect viruses (e.g. baculovirus); yeast vectors; bacteriophage vectors (e.g. lambda phage); plasmid vectors such as pcDNA3 and cosmid vectors. Preferred expression vectors suitable for the invention are adenoviral vector such as helper-dependent adenoviral vectors and lentiviral vectors.

Another object of the invention is a pharmaceutical composition comprising at least one selective inhibitor of c-Fos for use for preventing and/or treating
  a cancer selected in the group consisting of colon cancer, pancreatic cancer, melanoma, ovary cancer, lung cancer, thyroid cancer, leukaemia, juvenile myelomonocytic leukaemia, glioma, neurofibroma, cervical hepatocarcinoma, breast cancer, osteosarcoma and endometrial cancer; and/or
  neurofibromatosis, preferably neurofibromatosis I (NF1).

In one embodiment of the invention, said pharmaceutical composition comprises:
  a) at least one selective inhibitor of c-Fos as described here above;
  b) a nucleic acid encoding said peptide as described here above; or
  c) an expression vector comprising said nucleic acid as described here above.

The selective inhibitor of c-Fos of the invention, nucleic acid sequences encoding thereof or expression vectors comprising said nucleic acid sequences can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Prescription of treatment, e. g. decisions on dosage etc, is within the responsibility of general practitioners and other medical doctors, and typically takes account of the disorder to be treated, the condition of the individual patient, the site of delivery, the method of administration and other factors known to practitioners.

In a therapeutic application, the selective inhibitor of c-Fos of the invention are embodied in pharmaceutical compositions intended for administration by any effective means, including parenteral, topical, oral, pulmonary (e.g. by inhalation) or local administration.

Preferably, the pharmaceutical compositions are administered parenterally, e.g., intravenously, subcutaneously, intradermally, or intramuscularly, or intranasally.

In one embodiment of the invention, the pharmaceutical composition of the invention is administrated by intranasal route.

In another embodiment of the invention, the pharmaceutical composition of the invention is administrated intravenously.

In one embodiment, peptides that have the ability to cross the blood brain can be administered, e.g., systemically, nasally, etc., using methods known to those of skill in the art. In another embodiment, larger peptides that do not have the ability to cross the blood brain barrier can be administered to the mammalian brain via intracerebroventricular (ICV) injection or via a cannula using techniques well known to those of skill in the art.

In one embodiment, the invention provides compositions for parenteral administration that comprise a solution of peptide of the invention, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the NAP or ADNF polypeptides are preferably supplied in finely divided from along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., J Mol Neurosci. 19(1-2):167-70 (2002)).

Another object of the invention is a method for preventing and/or treating cancer in a subject in need thereof, said method comprising administering a therapeutically effective amount of at least one selective inhibitor of c-Fos as described here above, or a therapeutically effective amount of a pharmaceutical composition as described here above.

All the previously mentioned technical data are applicable here.

In one embodiment, the selective inhibitor of c-Fos of the invention is administered to a patient in an amount sufficient to prevent and/or treat cancer. An amount adequate to accomplish this is defined as "therapeutically effective dose". Amounts effective for this use will depend on, for example, the particular peptide inhibitor employed, the type of disease or disorder to be prevented, the route of administration, the weight and general state of health of the patient, and the judgement of the prescribing physician.

For example, an amount of peptide inhibitor falling within the range of a 100 ng to 10 mg dose given intranasally once a day (e.g., in the evening) would be a therapeutically effective amount. Alternatively, dosages may be outside of this range, or on a different schedule. For example, dosages may range from 0.0001 mg/kg to 10,000 mg/kg, and will preferably be about 0.001 mg/kg, 0.1 mg/kg, 1 mg/kg 5 mg/kg, 50 mg/kg or 500 mg/1 g per dose. Doses may be administered hourly, every 4, 6 or 12 hours, with meals, daily, every 2, 3, 4, 5, 6, for 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated.

In one embodiment, the invention relates to a method for preventing and/or treating a cancer selected in the group consisting of colon cancer, pancreatic cancer, melanoma, ovary cancer, lung cancer, thyroid cancer, leukaemia, juvenile myelomonocytic leukaemia, glioma, neurofibroma, cervical hepatocarcinoma, breast cancer, osteosarcoma and endometrial cancer in a subject in need thereof, and/or neurofibromatosis, said method comprising administering a therapeutically effective amount of at least one selective inhibitor of c-Fos wherein said peptide comprises at least one cell penetrating sequence, and an amino acid sequence corresponding to a docking domain sequence of c-Fos comprising SEQ ID NO: 29 (FVFTYPEA).

The invention also relates to a method for inhibiting and/or preventing the proliferation of a cell line selected in the group consisting of vascular smooth muscle cells, fibroblasts, and nerve sheath cells, said method comprising administering a therapeutically effective amount of at least selective inhibitor of c-Fos, wherein said peptide comprises at least one cell penetrating sequence, and an amino acid sequence corresponding to a docking domain sequence of c-Fos comprising SEQ ID NO: 29 (FVFTYPEA).

The invention also relates to a method for preventing metastasis, a method for inhibiting and/or preventing proliferation of cells on a stent and a method for preventing and/or treating neurofibromatosis. All the technical data previously disclosed arte applicable here.

FIGURES

FIG. 1: Schema summarizing the Ras-ERK signalling pathway and mutations in human cancers.

FIG. 2: Concept of the Pepsignal.

Panel A depicts the mechanism of action of classical MEK inhibitors used so far. They act upstream of ERK and block the activation of all ERK substrates without discrimination.

Panel B illustrates the particularity of the "pepsignal" that are the only bio-molecule acting downstream from ERK. They mimic the DEF docking domain of a given substrate towards ERK, and as such have a very specific inhibitory impact of a given substrate of interest.

Figure 3:
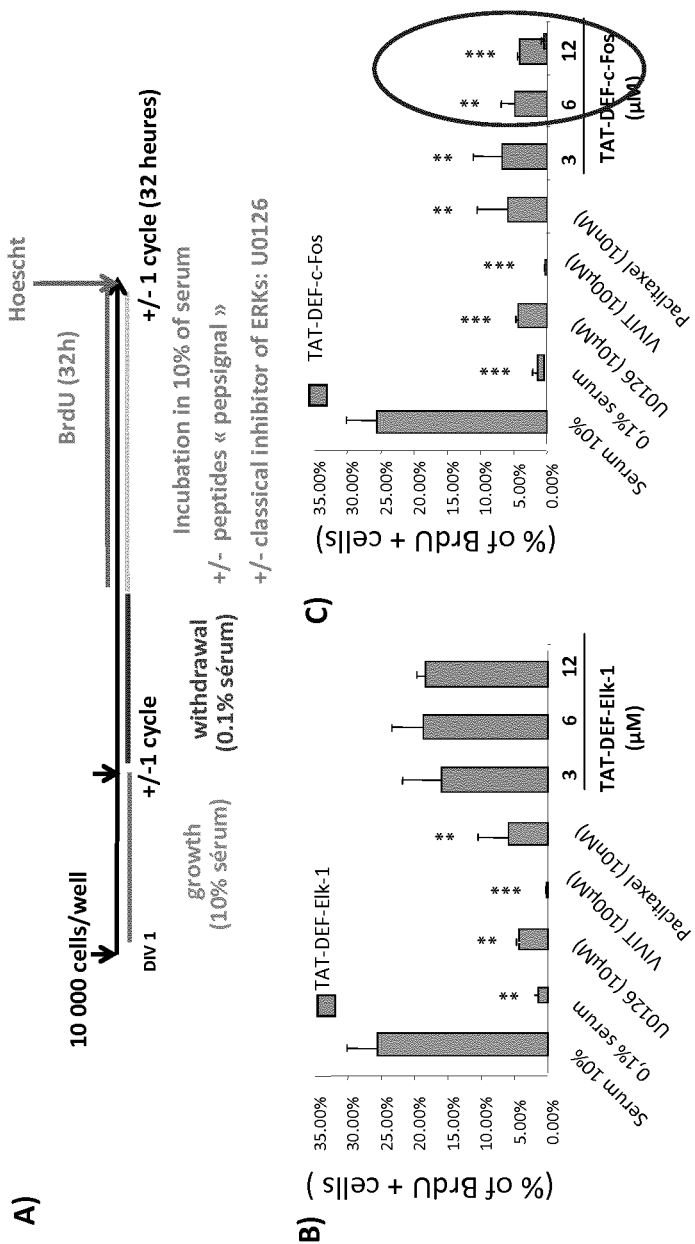

FIG. 3: The peptide of the invention TAT-DEF-c-Fos, blocks serum-induced proliferation of vSMC cells whereas the peptide TAT-DEF-Elk-1 does not.

On day one, 10 000 cells per well were grown in the presence of 10% serum. After one cycle of cell division (around 32 hours), the cells were starved (0.1% serum), then they were grown in 10% FBS (serum) in the presence or not of either the TAT-DEF-Elk-1, the TAT-DEF-c-Fos or classical inhibitors of cell proliferation (U0126, an ERK inhibitor; VIVIT or Paclitaxel) in the presence of BrdU for 32 h to label dividing cells. On the bases of our previous results in neuronal cells (see Lavaur et al., 2007) three different doses of pepsignal were tested: from 3 to 12 µM. Note that the TAT-DEF-c-Fos but not TAT-DEF-Elk-1 is efficient in the inhibition of vSMC proliferation; n=3; One-way ANOVA; Dunett post hoc test;  $p<0.01$; * $p<0.001$ when compared to the group treated with 10% serum FIG. 4: Efficacy of the peptide of the invention TAT-DEF-c-Fos on the inhibition of serum-induced proliferation of vSMC cells: comparison of single and multiple applications.

Using the same protocol as in FIG. 3, cells were grown in the presence of 10% FBS (serum) after withdrawal. The peptide TAT-DEF-c-Fos was applied once (6 or 12 µM) on day one (first day after withdrawal) and proliferation was tested using a BrdU assay 24, 48 or 72 hours later. When indicated, multiple applications of the peptide were done ("m") every 24 hours. Note that the TAT-DEF-c-Fos12 µM is not reported herein; n=3; Two-way ANOVA; Bonferroni post hoc test; *** $p<0.001$ when compared to the group treated with 10% serum.

Figure 5:
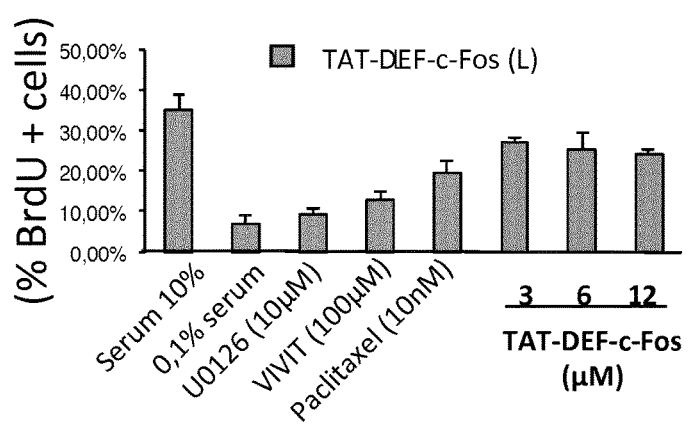

FIG. 5: TAT-DEF-c-Fos is devoid of anti-proliferative properties on HCAEC.

Using the same protocol than in FIG. 3, cells were grown in the presence of 10% serum after withdrawal. The peptide TAT-DEF-c-Fos was applied at a single dose one day after withdrawal. Proliferation was tested using a BrdU assay; n=3; One-way ANOVA; Dunett post hoc test; * p<0.05; when compared to the group treated with 10% serum FIG. 6: Antiproliferative properties of TAT-DEF-c-Fos on NIH3T3 cells On day one, 10 000 cells per well were grown in the presence of 10% serum. After one cycle of cell division (around 22 hours), the cells were starved (0.1% serum), then they were grown in 10% serum in the presence or not of the TAT-DEF-c-Fos (1,3,6, or 12 µM) or classical inhibitors of cell proliferation (U0126, an ERK inhibitor; VIVIT or Paclitaxel) in the presence of BrdU for 3 h to labelled dividing cells. Bars are the mean % of BrdU positive cells obtained from two experiments performed with 2 different stainings of NIH3T3 cells.

Figure 7:
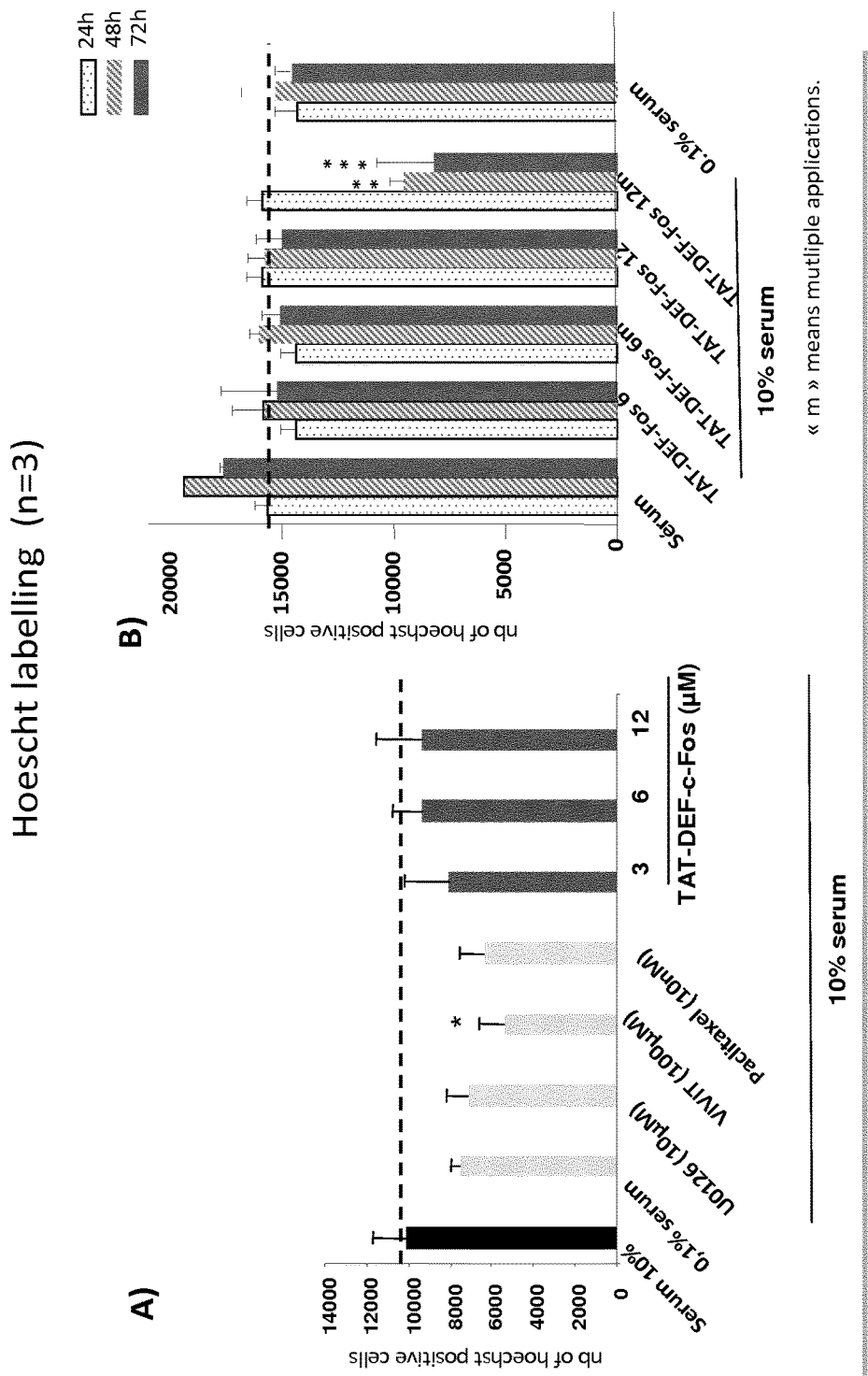

FIG. 7: TAT-DEF-C-Fos toxicity on vSMC

Cell viability was tested using an Hoechst staining at the end of the indicated time after 10% serum application. A) the peptide was applied at 3; 6 or 12 µM. the cells were fixed 24 hours after the serum application. B) The cells were fixed 24, 48 or 72 hours after serum application. When indicated, multiple applications of the peptide were done ("m") every 24 hours. Note that the TAT-DEF-c-Fos12m is not reported, as it was toxic at this dose after multiple applications. The number of Hoechst positive cells was counted after acquisition of the image and automatized counting was performed, using a dedicated software (Image Pro). Statistics: Two way ANOVA followed by a bonferroni test *p<0.05; p<0.01; *p<0.001 when compared to 24 hours FIG. 8: Inhibitory role of TAT-DEF-c-Fos peptides in the wound-healing test in vSMC.

The peptide was applied once, at the same time as 10% serum. The invasiveness was calculated as the percentage of cells over the size of the lesion, 24, 48 and 72 hours post-lesion. Note the lack of effect of the global MEK inhibitor (U0126), note also the inhibitory role of the TAT-DEF-c-Fos peptide at 12 µM whatever the time point chosen.

Figure 9:
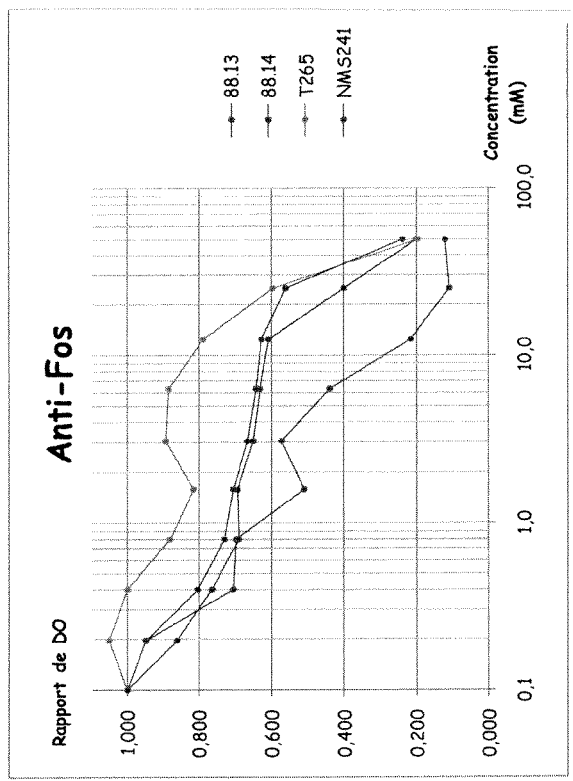
Figure 9:
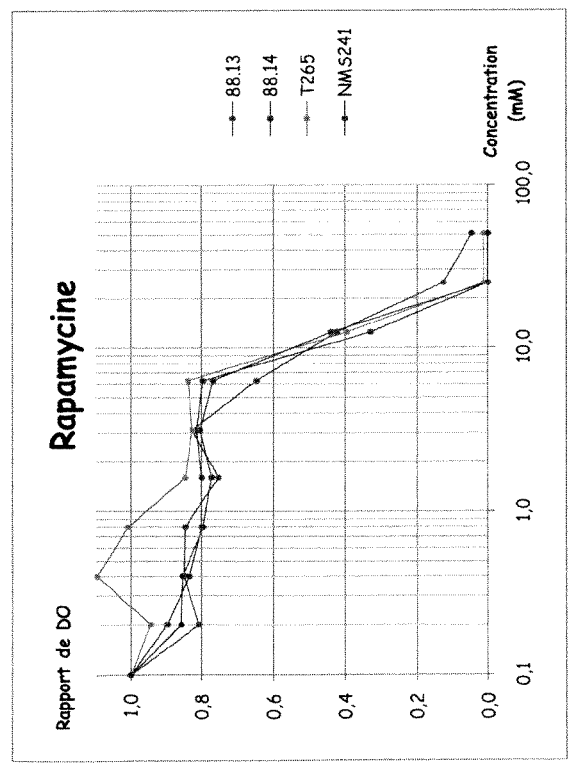

FIG. 9: Comparative effects TAT-DEF-c-Fos and Rapamycin on MPNST from NF1 patients Human cell lines from malignant peripheral nerve sheat tumors (MPNST) were treated with either TAT-DEF-c-Fos at increasing doses, or as a control, with Rapamycin, an inhibitor of the mTOR pathway that is classically used as an inhibitor of proliferation on this cell line. The TAT-DEF-c-Fos peptide inhibited proliferation of MPNST at very low doses when compared to Rapamycin (IC50 for TAT-DEF-c-Fos around 10 µM instead of 10 mM for Rapamycin). This indicates that the peptide is highly efficient on the inhibition of proliferation on this malignant cell line.

Figure 10:
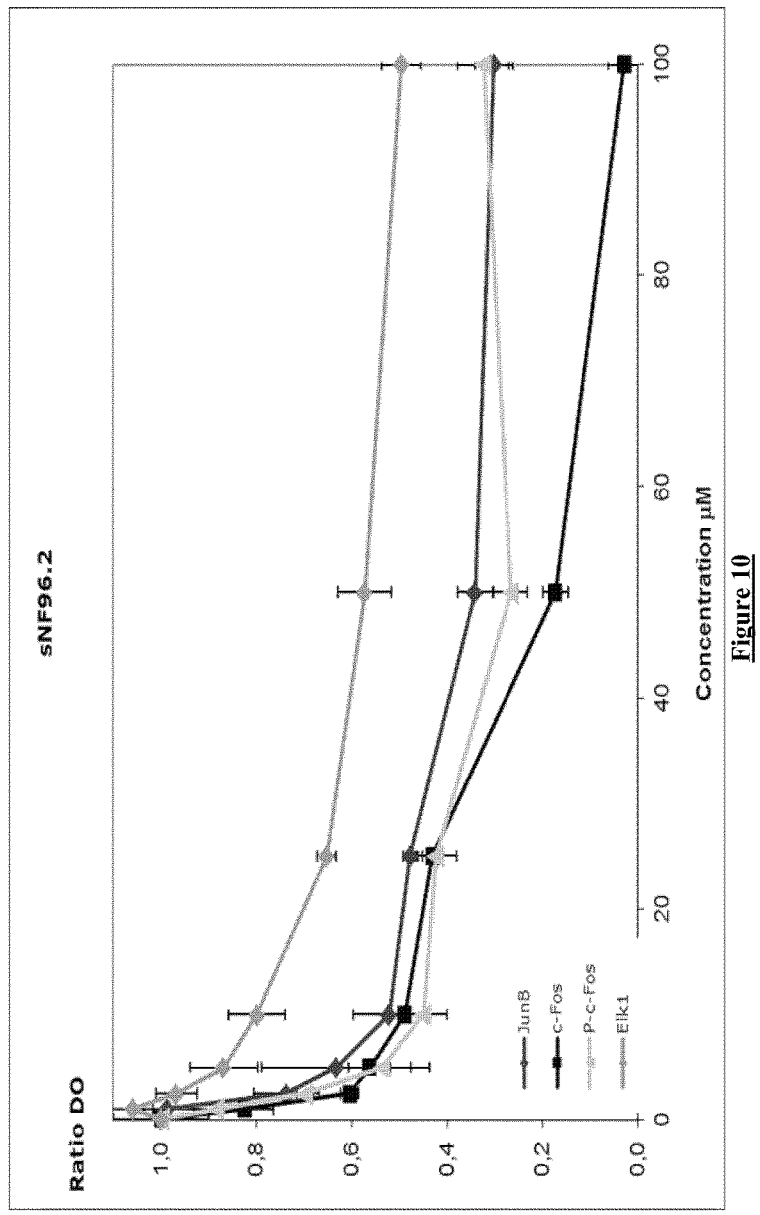

FIG. 10: Inhibitory effects of 4 different peptides on sNF96.2

4 different peptides are tested on malignant Peripheral Nerve Sheath Tumors (MPNST) cell lines, as follows:

Peptide TAT-DEF-c-Fos;

Peptide TAT-DEF-Elk-1;

Peptide TAT-DEF-JunB; and

Peptide Penetratin-DEF-c-Fos.

EXAMPLES

Example 1

Anti-proliferative Property of TAT-DEF-c-Fos Peptide on vSMC, MPNST from NF1 Patients and NIH3T3 Cell Lines Methods Cell Lines Primary vascular smooth muscle cells (vSMC) (ATCC CRL-1999) were grown in DMEM F12K medium supplemented 0.05 mg/ml ascorbic acid; 0.01 mg/ml insulin; 0.01 mg/ml transferrin; 10 ng/ml sodium selenite; 10% (v/v) heat-inactivated FBS (Fetal Bovine Serum), 100 U/ml penicillin, and 100 µg/ml streptomycin, 10 mM HEPES.

Primary human coronary arterial endothelial cells (HCAEC) (Promocell C12222) were grown in Endothelial Cell Growth Medium MV2 (Promocell).

NIH 3T3 mouse embryonic fibroblast cells were grown in DMEM supplemented with 10% (v/v) heat-inactivated FBS, 100 U/ml penicillin, and 100 µg/ml streptomycin.

Malignant Peripheral Nerve Sheath Tumors (MPNST: from NF1 patients) were obtained from Michel Videaud's laboratory. 2000 cells were grown in the presence of 15% serum after withdrawal.

Cultures were maintained at 37° C. in humidified 95% air and 5% CO2

Pharmaceutical Compounds

The compounds used by the inventors are as follows:

U0126 was from Tocris. Paclitaxel was from Millipore.

```
TAT-DEF-c-Fos:
sequence
                                    (SEQ ID NO: 26)
GRKKRRQRRRPPCTTYTSSFVFTYPEADSFP;
and sequence
                                    (SEQ ID NO: 36)
GRKKRRQRRRPPCTTYTSSFVFTYPEADSFPS;

TAT-DEF-Elk-1:
sequence
                                    (SEQ ID NO: 27)
GRKKRRQRRRPPSPAKLSFQFPSSGSAQVHI;
and VIVIT:
sequence
                                    (SEQ ID NO: 28)
MAGPHPVIVITGPHEE.
```

TAT-DEF-Elk-1 and TAT-DEF-c-FOS peptides were synthesized under their L conformation using "Fmoc solid-phase peptide synthesizer" by Genecust.

Peptides were purified by HPLC (>99%) and analyzed by matrix-assisted laser desorption ionization time-of-flight mass spectrometry (MALDI-TOF MS). Stock solution (1 mM) were prepared in sterilized water and stored until use at −20° C.

Proliferation and Toxicity Assay 10 000 cells per well were grown in the presence of complete medium. After one cycle of cell division (around 32 hours for HCAEC and vSMC, 24 hours for NIH3T3), the cells were starved for one other cycle (0.1% serum or nutriment supplement for HCAEC). Then they were grown in complete medium in the presence or not of each of the "Pepsignal" (3, 6 or 12 µM), the MEK inhibitor U0126 (10 µM), or classical inhibitors of cell proliferation Paclitaxel (10 nM), VIVIT (100 μM) for 24 to 72 hours. Proliferation was analyzed after BrdU incorporation, which allows the visualization of cells under division. For HCAEC and vSMC, BrdU was added with inhibitor. For NIH3T3, it was added only during the last three hours. Cells were fixed in 4% paraformaldehyde.

Toxicity was analyzed by Hoechst staining after fixation, which allows the labeling of all nuclei, and hence their quantification. Only the nuclei with an intact nucleus were taken into account. Image-Pro Plus software (Media Cybernetics) was used in order to quantify BrdU positive cells. The percentage of positive cells was reported to the total number of Hoechst-positive cells.

Wound Healing Assay

Cells were cultured in 24-well plates as a confluent monolayer (30000 cells plated per well). The monolayer was starved in 0,1% serum (or nutriment supplement for HCAEC) for 24 hours and wounded in a line across the well with a 200-μl pipette tip, then incubated with 10% serum (or nutriment supplement for HCAEC), in the presence or absence of U0126 (10 μM), Paclitaxel (10 nM/l), VIVIT (100 μM) or TAT-DEF-c-FOS (3,6,12 μM) for 24 to 72 hours. Cells were fixed in 4% paraformaldehyde then stained with cresyl violet dye (1% in methanol). Pictures were taken to visualize the marked wound location. The wound healing effect was measured using the NIH ImageJ program and expressed as percentage of recovery of the lesion.

Results

1) Anti-proliferative Properties of TAT-DEF-c-Fos on vSMCs

The inventors first tested and compared the anti-proliferative properties of TAT-DEF-Elk-1, TAT-DEF-c-Fos, classical inhibitors of ERK, and classical inhibitors of cell proliferation on vSMC (FIG. 3). They used a classical protocol of cell proliferation induced by serum (10%) and BrdU incorporation. On the bases of our previous results in neuronal cells (see Lavaur et al., 2007) three different doses of pepsignal were tested: from 3 to 12 μM. The inventors found that TAT-DEF-c-Fos (but not TAT-DEF-Elk-1) had anti-proliferative properties at 3, 6 and 12 μM. Since results were more reproducible at the doses of 6 and 12 μM, other experiments were carried on with 6 or 12 μM. At 12 μM, this anti-proliferative effect was comparable to classical inhibitors of ERK, or inhibitors of cell proliferation classically used on this cell line (FIG. 3c).

Figure 4:
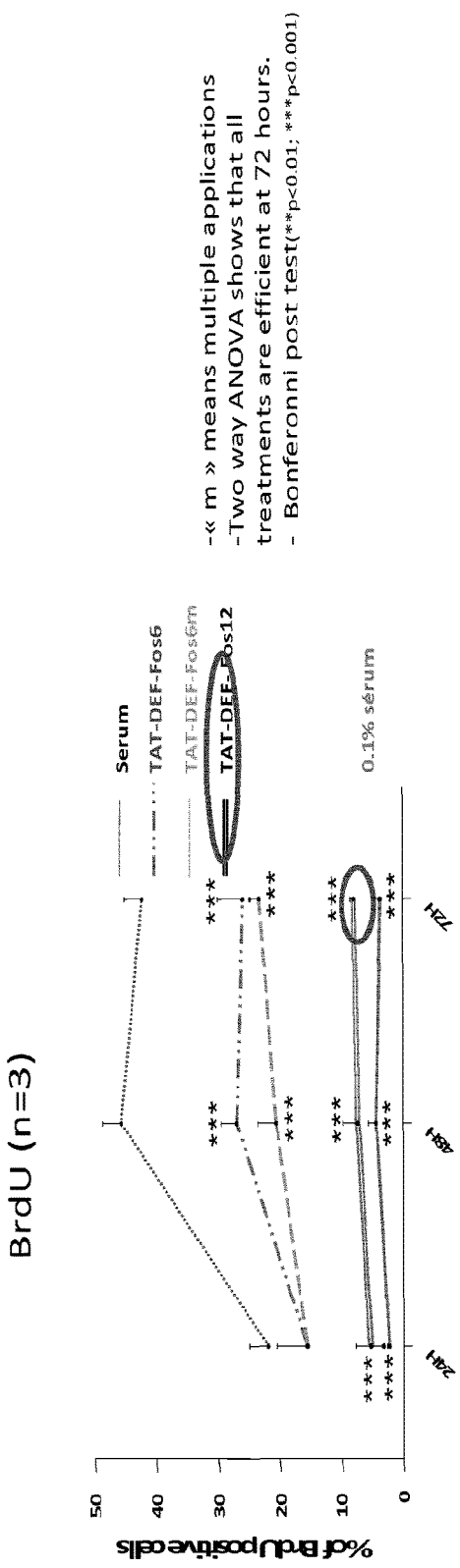

Having established that a unique application of the TAT-DEF-c-Fos was efficiently inhibiting the proliferation of vSMC, the inventors decided to determine its anti-proliferative properties after multiple cycles. In this experiment, single and multiple applications of the TAT-DEF-c-Fos peptide were tested. The inventors found that the TAT-DEF-c-Fos peptide was as efficient at single and multiple applications at 6 μM for inhibiting cell proliferation (FIG. 4). At the dose of 12 μM, one application of the peptide was necessary and sufficient to obtain rapidly (as soon as 24 hours) an inhibition of proliferation. At this dose, multiple applications were toxic.

Because anti-proliferative properties of a compound may be highly specific of a cell line and/or organ, depending on the extracellular stimuli and the environment, the inventors decided to test the efficacy of TAT-DEF-c-Fos on serum-induced proliferation of endothelial cells (HCAEC) (FIG. 5).

On this cell line, the classical inhibitors (VIVIT, Paclitaxel) of proliferation and ERK inhibitors (U0126) were efficient to inhibit HCAEC cell proliferation, but the TAT-DEF-c-Fos peptide was devoid of effect whatever the dose. This data thus indicates that the anti-proliferative properties of TAT-DEF-c-Fos are cell-specific.

2) Anti-proliferative Properties of TAT-DEF-c-Fos on Malignant NF1

The inventors tested the efficacy of TAT-DEF-c-Fos on malignant NF1 cell proliferation (FIG. 9). For this purpose, the inventors used Human cell lines from malignant peripheral nerve sheat tumors (MPNST) from NF1 patients.

The MPNST cell lines were derived from a recurrent mass associated with peripheral nerve sheat and diagnosed as MPNST (Malignant Peripheral Nerve Sheath Tumor) in patients meeting NF1 diagnostic criteria. The cells were derived from numerous passages of primary tumor material in culture until they were a homogenous Schwann cell-like population which displayed a clonal morphology immunopositive for both cytoplasmic Schwann cell markers S100 and p75.

As a control, the inventors chose Rapamycin, an inhibitor of the mTOR pathway that is classically used as an inhibitor of proliferation on this cell line. The TAT-DEF-c-Fos peptide inhibited proliferation of MPNST at very low doses when compared to Rapamycin (IC50 for TAT-DEF-c-Fos around 10 μM instead of 10 mM for Rapamycin). This indicates that the peptide is highly efficient on the inhibition of proliferation on this malignant cell line.

3) Anti-proliferative Properties of TAT-DEF-c-Fos on Fibroblasts

Figure 6:
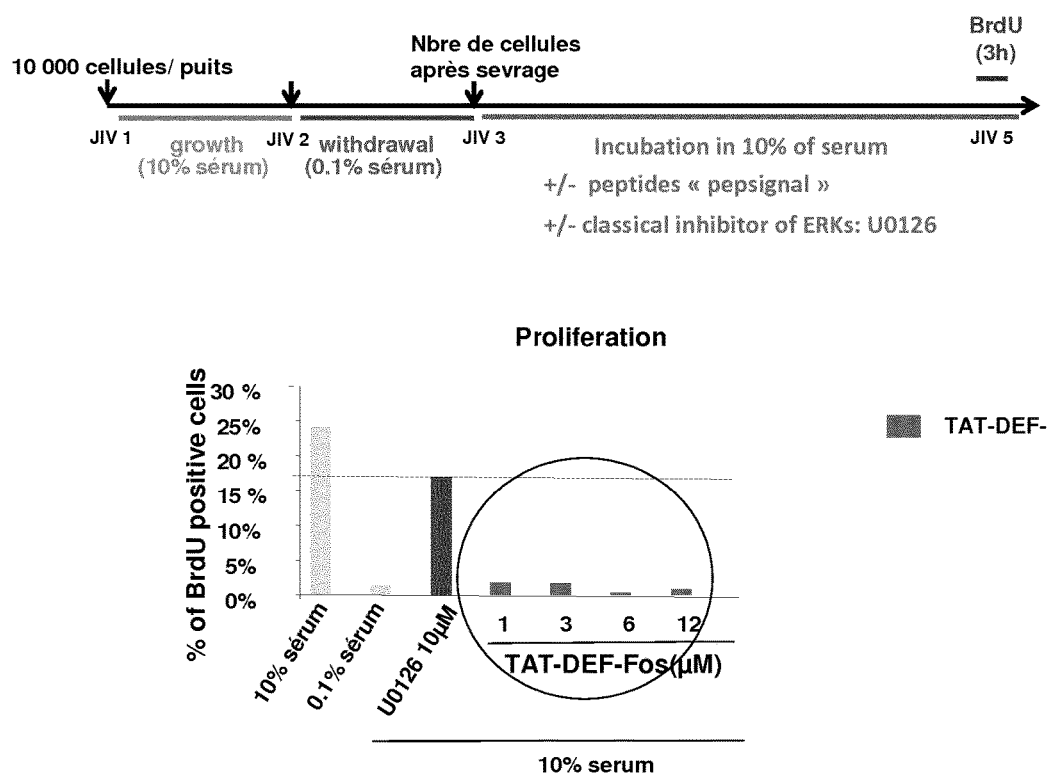

Next the inventors tested the efficacy of TAT-DEF-c-Fos peptide on fibroblasts (NIH3T3 cells) (FIG. 6). On this cell line, the efficacy of the TAT-DEF-c-Fos peptide was found at low doses (from 1 to 12 μM), while the ERK inhibitor U0126 failed to inhibit proliferation. This data indicates the specificity of ERK activity towards c-Fos on fibroblast proliferation.

4) The TAT-DEF-c-Fos is Devoid of Toxicity

Classical inhibitors of proliferation, a MEK inhibitor or the TAT-DEF-c-Fos peptide at increasing doses were applied on vSMCs, in the presence of 10% serum, on a single application (FIG. 7A) and toxicity was evaluated after PFA fixation and Hoechst staining. Counting of viable cells was performed and expressed as number of Hoechst positive cells (showing nuclear labelling integrity). Contrasting with the classical inhibitor of cell proliferation on this cell line (VIVIT) that showed toxicity (decreased number of viable cells), no toxicity was observed in the presence of TAT-DEF-c-Fos at the doses used for inhibiting cell proliferation (from 3 to 12 μM) (see FIG. 3B). The inventors also evaluated the toxicity of TAT-DEF-c-Fos after multiple applications (FIG. 7B). On this experiment, the peptide was applied every 24 hours in the presence of serum. The cells were fixed and stained with Hoechst at 24, 48 or 72 hours. At 6 μM, the peptide did not alter the number of Hoechst positive cells whatever the number of applications. At 12 μM, it showed toxicity after 48 and 72 hours.

5) The TAT-DEF-c-Fos has Anti-Invasive Properties on vSMC

Invasive properties were studied using the wound healing protocol.

Figure 8:
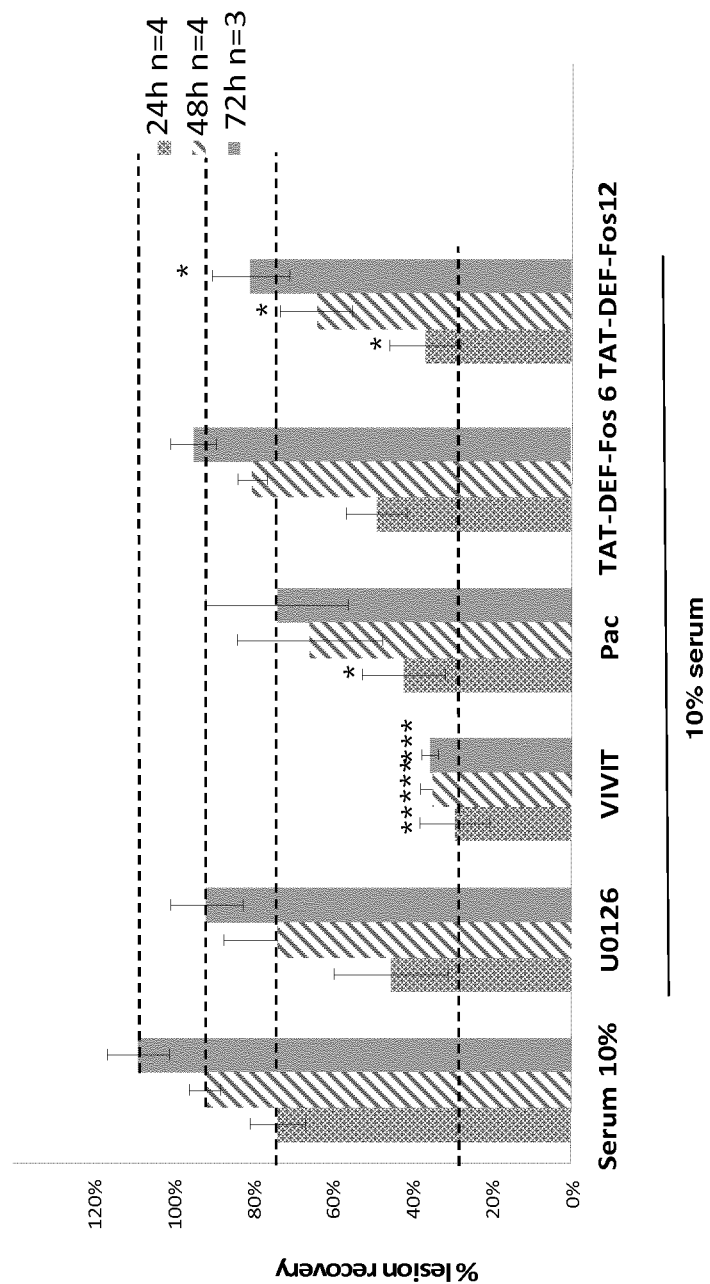

The percentage of lesion recovery was measured after cresyl violet staining of vSMC cells (FIG. 8). At 24 hours, the reference compound VIVIT showed a significant inhibition of invasiveness (around 30% recovery versus 78% in the presence of serum only). This inhibition was sustained since it was still significant after 78 hours of serum application (35% recovery versus 110% in the presence of serum only). However due to its toxic effect, this inhibition may be related to cell death.

Paclitaxel had a significant but transient effect on vSMC invasiveness. Whatever the doses used, the classical MEK inhibitor failed to block invasiveness. By contrast, the inventors found a significant effect of the TAT-DEF-c-Fos peptide at 12 μM at the different time points (FIG. 8). Despite a tendency at 24 hours, the TAT-DEF-c-Fos peptide had no significant effect on cell invasiveness at 6 μM.

Conclusion:

The TAT-DEF-c-Fos peptide has anti-proliferative properties on vSMC, PNMT and NIH3T3 cell lines.

Its efficacy is dose-dependent, but it becomes toxic at higher doses after multiple applications.

The TAT-DEF-c-Fos inhibits invasiveness.

The TAT-DEF-c-Fos peptide has specific properties when compared to TAT-DEF-Elk-1 or global MEK inhibitors.

Example 2

Comparative Properties of TAT-DEF-c-Fos, TAT-DEF-Elk-1, TAT-DEF-JunB, Penetratin-DEF-c-Fos on Proliferation of Malignant NF1 Cells (MPNST)

Method

The inventors have further tested 4 different peptides in the Peripheral Nerve Sheath Tumors (MPNST) cell lines sNF96.2, which was deposited to the ATCC under the reference ATCC® CRL-2884™.

The compounds used by the inventors are as follows:

```
Peptide TAT-DEF-c-Fos:
                                       (SEQ ID NO: 36)
GRKKRRQRRRPPCTTYTSSFVFTYPEADSFPS;

Peptide TAT-DEF-Elk-1:
                                       (SEQ ID NO: 27)
GRKKRRQRRRPPSPAKLSFQFPSSGSAQVHI;

Peptide TAT-DEF-JunB:
                                       (SEQ ID NO: 37)
GRKKRRQRRRPPTTPTPPGQYFYPRGGGSGGGAG;

Peptide Penetratin-DEF-c-Fos:
                                       (SEQ ID NO: 38)
RQIKIWFWNRRMKWKKPPCTTYTSSFVFTYPEADSFPS.
```

Cells were cultured at Day0 in a complete medium (DMEM with 10% of fetal bovine serum). Then they were deprived at Day2 (24 hours in a medium comprising DMEM with 0.1% fetal bovine serum followed by 24 hours in DMEM alone).

At Day 4, the cells were incubated with a dose escalation regimen of pepsignal peptides from 2 to 100 μM.

The proliferation tests were carried out 96 hours later.

Proliferation was analysed by a MTT assay. The MTT assay is a colorimetric assay for assessing cell viability. The viability is measured by the metabolic activity if the cells, which is determined by the activity of a mitochondrial succinate dehydrogenate. Typically, the cell media goes from yellow to blue and the intensity of the coloration is proportional to the number of viable cells. Coloration is determined by atomic absorption spectrometry at 570 nm.

Results

The inventors performed three independent experiments, each point being performed in duplicate for each experiment.

The results are illustrated on FIG. 10 and summarized as follows:

The IC50 of TAT-DEF-c-Fos is approximatively of 10 μM (FIG. 10). At a concentration of 100 μM, the peptide shows total inhibition.

The peptide Penetratin-DEF-c-Fos shows anti proliferative properties on MPNST (FIG. 10), with however lower efficacy than the TAT-DEF-c-Fos peptide (approximatively 66% of inhibition at a concentration of 100 μM).

The peptide TAT-DEF-JunB also shows anti proliferative properties, with lower efficacy than the TAT-DEF-c-Fos peptide.

Finally, the peptide TAT-DEF-Elk1 has low anti-proliferative properties (FIG. 10). The inhibition of proliferation does not reach 50%, even at higher doses.

Conclusion

In conclusion, the peptides TAT-DEF-c-Fos and Penetratin-DEF-c-Fos both show an inhibitory effect on MPNST. However, TAT-DEF-c-Fos shows higher efficacy.

In addition, TAT-DEF-Junb and TAT-DEF-Elk-1 shows effects, which are well below the effects conveyed by TAT-DEF-c-Fos.

Finally, the results of the inventors show that a peptide bearing a TAT sequence

The invention claimed is:

1. A selective inhibitor of c-Fos for use in the prevention and/or treatment of a cancer
   caused by or involving a mutation in the Ras/ERK pathway; and/or
   associated with an increased production of c-Fos;
   wherein said selective inhibitor of c-Fos is a peptide comprising:
   at least one cell penetrating sequence, and
   an amino acid sequence corresponding to a docking domain sequence of c-Fos comprising SEQ ID NO: 29 (FVFTYPEA).

2. The selective inhibitor of c-Fos for use according to claim 1, wherein said cancer caused by or involving a mutation in the Ras/ERK pathway is caused by or involves a mutation of Raf or Ras.

3. The selective inhibitor of c-Fos for use according to claim 2, wherein said cancer is selected from the group consisting of: colon cancer, pancreatic cancer, melanoma, thyroid cancer, lung cancer, leukaemia, and ovary cancer.

4. The inhibitor peptide of c-Fos for use according to claim 1, wherein said cancer caused by or involving a mutation in the Ras/ERK pathway is caused by or involves a mutation of NF1.

5. The selective inhibitor of c-Fos for use according to claim 4, wherein said cancer is selected from the group consisting of: glioma, juvenile myelomonocytic leukaemia and neurofibroma.

6. The inhibitor peptide of c-Fos for use according to claim 1,
   wherein said cancer associated with an increased production of c-Fos is selected from the group consisting of: cervical hepatocarcinoma, pancreatic cancer, breast cancer, osteosarcoma, and endometrial cancer.

7. A selective inhibitor of c-Fos for use in a method of preventing metastasis, wherein said selective inhibitor of c-Fos is a peptide comprising:
   at least one cell penetrating sequence; and
   an amino acid sequence corresponding to a docking domain sequence of c-Fos comprising SEQ ID NO: 29 (FVFTYPEA).

8. A selective inhibitor of c-Fos for use in inhibiting and/or preventing proliferation of vascular smooth muscle cells on a stent, wherein said selective inhibitor of c-Fos is a peptide comprising:
   at least one cell penetrating sequence; and
   an amino acid sequence corresponding to a docking domain sequence of c-Fos comprising SEQ ID NO: 29 (FVFTYPEA);
   and wherein said stent is used for treating a patient suffering from cardiovascular disease.

9. A selective inhibitor of c-Fos for use according to claim 8, wherein said stent is a drug-eluting stent.

10. A selective inhibitor of c-Fos for use in the prevention and/or treatment of neurofibromatosis, wherein said selective inhibitor of c-Fos comprises at least one cell penetrating sequence, and an amino acid sequence corresponding to a docking domain sequence of c-Fos comprising SEQ ID NO: 29 (FVFTYPEA).

11. The selective inhibitor of c-Fos for use according to claim 1, wherein said amino acid sequence corresponding to a docking domain sequence of c-Fos is selected from the group consisting of:

(SFVFTYPEAD), SEQ ID NO: 30

(SSFVFTYPEADS), SEQ ID NO: 31

(TSSFVFTYPEADSF), SEQ ID NO: 32

(YTSSFVFTYPEADSFP), SEQ ID NO: 33

(TYTSSFVFTYPEADSFP), SEQ ID NO: 34

(TTYTSSFVFTYPEADSFP), SEQ ID NO: 35

(CTTYTSSFVFTYPEADSFP), and SEQ ID NO: 1

(CTTYTSSFVFTYPEADSFPS). SEQ ID NO: 39

12. The selective inhibitor of c-Fos for use according to claim 1, wherein said amino acid sequence corresponding to a docking domain sequence of c-Fos is SEQ ID NO: 39 (CTT YTS SF VFT YPEAD SFPS).

13. The selective inhibitor of c-Fos for use according to claim 1, wherein said cell penetrating sequence is chosen from the group consisting of:
 HIV-TAT sequence (SEQ ID NO: 2);
 Penetratin (SEQ ID NO: 3);
 an amino acid sequence of 7 to 11 arginines (SEQ ID NO: 4 to 8);
 a X7/11R sequence of 7 to 25 amino acids comprising 7 to 11 arginines randomly positioned in the sequence; and
 a sequence derived from DPVs (SEQ ID NO: 13 to 17).

14. The selective inhibitor of c-Fos for use according to claim 1, wherein said peptide has the sequence SEQ ID NO: 26 (GRKKRRQRRRPPCTTYTSSFVFTYPEADSFP) or SEQ ID NO: 36 (GRKKRRQRRRPPCTTYTSS-FVFTYPEADSFPS).

15. A pharmaceutical composition for use in preventing and/or treating:
 a cancer selected from the group consisting of: colon cancer, pancreatic cancer, melanoma, ovary cancer, lung cancer, thyroid cancer, leukaemia, juvenile myelomonocytic leukaemia, glioma, neurofibroma, cervical hepatocarcinoma, breast cancer, osteosarcoma and endometrial cancer; and/or
 neurofibromatosis,
wherein, said pharmaceutical composition comprises:
 a) at least one selective inhibitor of c-Fos as defined in claim 1;
 b) a nucleic acid encoding said peptide; or
 c) an expression vector comprising said nucleic acid.

16. A selective inhibitor of c-Fos for use in the prevention and/or treatment of peripheral nerve sheath tumors, wherein said selective inhibitor of c-Fos comprises at least one cell penetrating sequence and an amino acid sequence corresponding to a docking domain sequence of c-Fos comprising SEQ ID NO: 29 (FVFTYPEA).

17. A pharmaceutical composition for use in preventing and/or treating neurofibromatosis I, wherein said pharmaceutical composition comprises:
 a) at least one selective inhibitor of c-Fos as defined in claim 1;
 b) a nucleic acid encoding said peptide; or
 c) an expression vector comprising said nucleic acid.

18. The selective inhibitor of CFOS for use according to claim 1, wherein said cell penetrating sequence is SEQ ID NO:9.

19. The selective inhibitor of CFOS for use according to claim 1, wherein said cell penetrating sequence is SEQ ID NO:10.

20. The selective inhibitor of CFOS for use according to claim 1, wherein said cell penetrating sequence is SEQ ID NO:11.

21. The selective inhibitor of CFOS for use according to claim 1, wherein said cell penetrating sequence is SEQ ID NO:12.

* * * * *